(12) United States Patent
Ascher et al.

(10) Patent No.: US 7,485,632 B2
(45) Date of Patent: *Feb. 3, 2009

(54) CEPHALOSPORINS

(75) Inventors: Gerd Ascher, Kundl (AT); Werner Heilmayer, Mödling (AT); Michael Schranz, Vienna (AT); Josef Wieser, Polling (AT)

(73) Assignee: Nabriva Therapeutics Forschungs GmbH, Wienn (AT)

( * ) Notice: Subject to any disclaimer, the term of this patent is extended or adjusted under 35 U.S.C. 154(b) by 264 days.

This patent is subject to a terminal disclaimer.

(21) Appl. No.: 10/527,882

(22) PCT Filed: Jul. 14, 2003

(86) PCT No.: PCT/EP03/07603

§ 371 (c)(1),
(2), (4) Date: Mar. 15, 2005

(87) PCT Pub. No.: WO2004/007505

PCT Pub. Date: Jan. 22, 2004

(65) Prior Publication Data

US 2005/0234233 A1 Oct. 20, 2005

(30) Foreign Application Priority Data

| Jul. 15, 2002 | (GB) | ................... | 0216418.4 |
| Sep. 24, 2002 | (GB) | ................... | 0222177.8 |
| Oct. 15, 2002 | (GB) | ................... | 0223974.7 |
| Oct. 15, 2002 | (GB) | ................... | 0223975.4 |
| Oct. 15, 2002 | (GB) | ................... | 0223976.2 |
| Oct. 15, 2002 | (GB) | ................... | 0223977.0 |

(51) Int. Cl.
C07D 501/24 (2006.01)
A61K 31/546 (2006.01)
A61P 31/04 (2006.01)

(52) U.S. Cl. ............... 514/202; 514/206; 544/222; 544/227

(58) Field of Classification Search ............... 514/202, 514/206; 540/227, 222
See application file for complete search history.

(56) References Cited

U.S. PATENT DOCUMENTS 6,531,465 B1 * 3/2003 Ascher et al. ............... 514/200

2006/0122164 A1 * 6/2006 Ascher et al. ............... 514/192

FOREIGN PATENT DOCUMENTS

| GB | 1 460 377 | 1/1977 |
| WO | 96/35692 | 11/1996 |

* cited by examiner

*Primary Examiner*—Mark L Berch
(74) *Attorney, Agent, or Firm*—D. Peter Hochberg; Sean F. Mellino; Daniel J. Smola

(57) ABSTRACT

A compound of formula

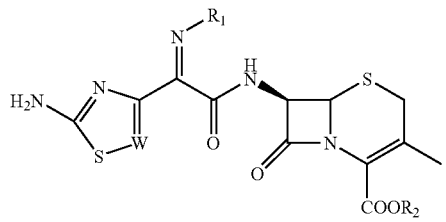

IA or of formula

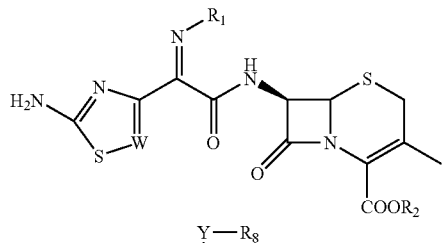

IB

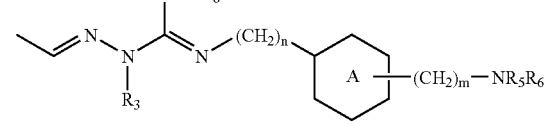

wherein the substituents have various meanings, useful as a pharmaceutical.

10 Claims, No Drawings

CEPHALOSPORINS

The present invention relates to cephalosporins.

In one aspect the present invention provides a compound of formula

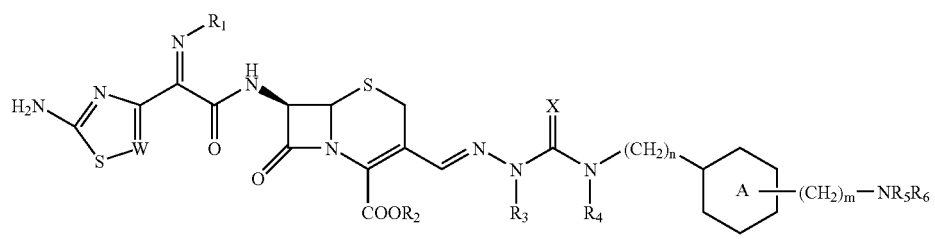

IA or of formula

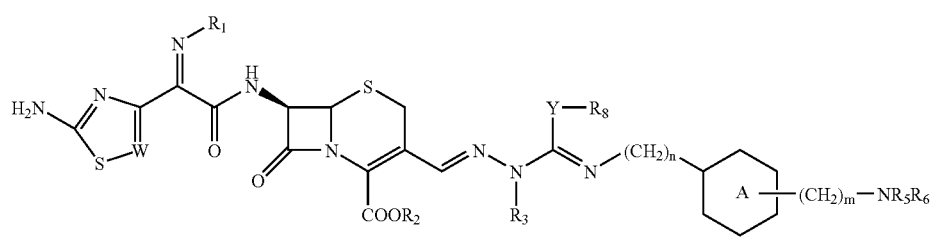

IB wherein

W is CH or N, $R_1$ is hydroxy, $(C_{1-6})$alkoxy, halo$(C_{1-6})$alkoxy, hydroxycarbonyl$(C_{1-6})$alkoxy or $(C_{1-6})$alkoxycarbonyl$(C_{1-6})$alkoxy, $R_2$ is hydrogen or an ester moiety, $R_3$ is hydrogen, $(C_{1-6})$alkyl, $(C_{2-6})$alkenyl or $(C_{2-8})$cycloalkyl, $R_4$ is hydrogen or $(C_{1-6})$alkyl,

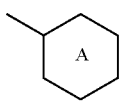

is cyclohexyl or phenyl, $R_5$ and $R_6$ independently of each other are hydrogen; $(C_{1-6})$alkyl; $(C_{2-6})$alkenyl;

$(C_{6-18})$arylcarbonyl; $(C_{1-6})$alkylcarbonyl; $(C_{6-18})$aryloxy$(C_{1-4})$alkylcarbonyl; $(C_{1-6})$alkylcarbonyl-$(C_{6-18})$arylcarbonyl; heterocyclyl$(C_{1-6})$alkylcarbonyl, wherein heterocyclyl comprises 5 or 6 ring members and 1 to 4 heteroatoms selected from N, O or S; $(C_{1-6})$alkylsulfonyl or $(C_{6-18})$arylsulfonyl, X is NH, O, S or N—$R_8$, wherein $R_8$ is $(C_{1-6})$alkyl or $(C_{3-8})$cycloalkyl, Y is O or S, and n and m independently of each other are 0 or 1.

In a compound of formula IA or IB preferably W, $R_1$, $R_3$, $R_4$, n, m and

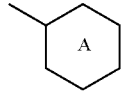

are as defined above, $R_2$ is hydrogen, $R_5$ and $R_6$ independently of each other are hydrogen; $(C_{1-6})$alkyl; $(C_{2-6})$alkenyl; $(C_{6-18})$arylcarbonyl, wherein aryl is optionally substituted by $(C_{1-4})$alkylcarbonyloxy; $(C_{6-18})$aryloxy$(C_{1-4})$alkylcarbonyl; heterocyclyl$(C_{1-6})$alkylcarbonyl, wherein heterocyclyl comprises 5 or 6 ring members and 1 to 4 heteroatoms selected from N, O or S; $(C_{6-18})$arylsulfonyl, wherein aryl is optionally substituted by amino or $(C_{1-4})$alkylcarbonylamino;

X is NH, O, S or N—$R_8$, wherein $R_8$ is $(C_{1-6})$alkyl or a group of formula

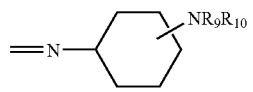

II wherein $R_9$ and $R_{10}$ have the meaning of $R_5$ and $R_6$ as defined above, and Y is S.

In a compound of formula IA or IB preferably n=0 and m=0, or n=1 and m=1, or n=1 and m=0.

In a compound of formula IA or IB each single defined substituent may be a preferred substituent, e.g. independently of each other substituent defined.

In another aspect the present invention provides a compound of formula IA or IB wherein W is CH or N, R$_1$ is hydroxy, methoxy, fluoromethoxy or (hydroxycarbonyl)(dimethyl)methoxy, R$_2$ is hydrogen, R$_3$ is hydrogen; (C$_{1-4}$)alkyl, e.g. methyl or ethyl; allyl or cyclopropyl, R$_4$ is hydrogen or (C$_{1-4}$)alkyl, e.g. methyl,

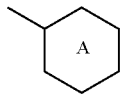

is cyclohexyl, e.g. and the —(CH$_2$)$_m$—NR$_5$R$_6$ group is in the ortho, meta or para position, R$_5$ and R$_6$ independently of each other are hydrogen;

(C$_{1-3}$)alkyl, e.g. methyl, ethyl, isopropyl or n-propyl;

allyl;

(C$_{1-4}$)alkylcarbonyl, e.g. methylcarbonyl;

phenylcarbonyl, wherein phenyl is optionally substituted by (C$_{1-4}$)alkylcarbonyloxy, e.g. methylcarbonyloxy;

phenoxymethylcarbonyl;

phenylsulfonyl, wherein phenyl is substituted by amino or(C$_{1-4}$)alkylcarbonylamino, e.g. methylcarbonylamino; or heterocyclyl comprising 5 ring members and 1 heteroatom selected from N, O or S, e.g. wherein heterocyclyl is aromatic heterocyclyl, e.g. thiophenyl, such as thiophenyl(C$_{1-4}$)alkylcarbonyl, e.g. thiophenylmethylcarbonyl;

X is NH, NCH$_3$, NCH(CH$_3$)$_2$, O, S or (C$_{3-8}$)cycloalkyl substituted by amino, such as cyclohexyl substituted by amino, e.g. in the para position, n is 0, m is 0, Y is S and R$_8$ is (C$_{1-4}$)alkyl, e.g. methyl.

In another aspect the present invention provides a compound of formula IA wherein W is N or CH, R$_1$ is hydroxy or fluoromethoxy, R$_2$, R$_4$, R$_5$ and R$_6$ are hydrogen, R$_3$ is (C$_{1-4}$)alkyl, e.g. methyl,

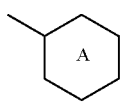

is cyclohexyl, e.g. and the —(CH$_2$)$_m$—NR$_5$R$_6$ group is in the meta or para position, X is NH, n is 1 and m is 1.

In another aspect the present invention provides a compound of formula IA wherein W is N, R$_1$ is fluoromethoxy, R$_2$, R$_4$, R$_5$ and R$_6$ are hydrogen, R$_3$ is (C$_{1-4}$)alkyl, e.g. methyl,

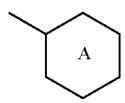

is phenyl, e.g. and the —(CH$_2$)$_m$—NR$_5$R$_6$ group is in the meta position, X is NH, n is 1 and m is 0.

In another aspect the present invention provides a compound of IA wherein

W is CH or N,

R$_1$ is hydroxy or fluoromethoxy,

R$_2$, R$_4$, R$_5$ and R$_6$ are hydrogen,

R$_3$ is (C$_{1-4}$)alkyl, e.g. methyl,

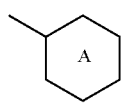

is phenyl, e.g. and the —(CH$_2$)$_m$—NR$_5$R$_6$ group is in the meta or para position, X is NH, n is 1 and m is 1.

In another aspect the present invention provides a compound of formula IA wherein W is N, R$_1$ is fluoromethoxy, R$_2$ is hydrogen or an ester moiety, R$_3$ is (C$_{1-4}$)alkyl, e.g. methyl, R$_4$, R$_5$ and R$_6$ are hydrogen,

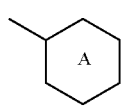

is cyclohexyl, e.g. and the —(CH$_2$)$_m$—NR$_5$R$_6$ group is in the para position, X is NH, n is 0 and m is 0.

In another aspect the present invention provides a compound of formula

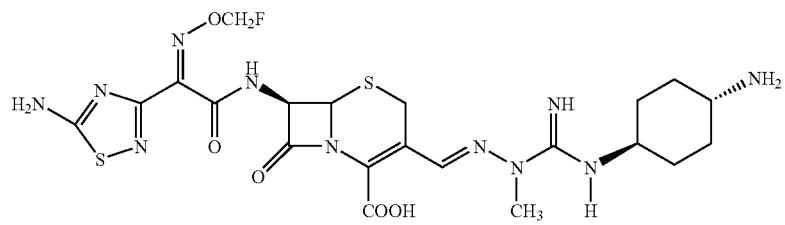

e.g. in the form of a hydrochloride.

An ester moiety as used herein includes alkyl; e.g. unsubstituted alkyl or substituted alkyl, e.g. by aryl, such as benzyl, alkoxybenzyl, such as 4-methoxybenzyl, alkoxy, such as methoxymethyl; alkyloxycarbonyloxy; alkyl; alkoxy, such as glycyloxy, phenylglycyloxy, e.g. glycyloxymethyl, phenylglycyloxymethyl; heterocyclyl e.g. 5-methyl-2-oxo-1,3-dioxolen-4-yl; indanyl, phthalidyl, alkoxycarbonyloxy and ester moieties which form with the COO⁻-group a physiologically hydrolysable and acceptable ester, e.g. such as known to be hydrolysable ester groups in the field of cephalosporins. A compound of formula I may thus be in the form of an physiologically-hydrolysable and -acceptable ester. By physiologically-hydrolysable and -acceptable esters as used herein is meant an ester in which the COO⁻-group is esterified and which is hydrolysable under physiological conditions to yield an acid which is itself physiologically tolerable at dosages to be administered. The term is thus to be understood as defining regular prodrug forms. An ester moiety may be preferably a group which is easily hydrolysable under physiological conditions. Such esters may be administered preferably orally. Parenteral administration may be indicated if the ester per se is an active compound or, if hydrolysis occurs in the blood.

If not otherwise defined herein, aryl includes $(C_{6-18})$aryl, e.g. phenyl. Any group(s) may be unsubstituted or one or morefold substituted, e.g. by groups as conventional in cephalosporin chemistry.

Compounds provided by the present invention are hereinafter designated as "compound(s) of (according to) the present invention". A compound of the present invention includes a compound in any form, e.g. in free form, in the form of a salt, in the form of a solvate and in the form of a salt and a solvate.

In another aspect the present invention provides a compound of the present invention in the form of a salt.

Such salts include preferably pharmaceutically acceptable salts, although pharmaceutically unacceptable salts are Included, e.g. for preparation/isolation/purification purposes.

A salt of a compound of the present invention includes a metal salts, acid addition salts, amine salts, and inner salts and quaternary salts, where possible. Metal salts include for example alkali or earth alkali salts, preferably sodium or potassium salts; acid addition salts include salts of a compound of formula I with an acid, e.g. hydrogen fumaric acid, fumaric acid, naphthalin-1,5-sulphonic acid, hydrochloric acid, deuterochloric acid; preferably hydrochloric acid.

Amine salts include for example trialkylamine, procaine, dibenzylamine and benzylamine salts, e.g.the amine group attached to the ring of formula

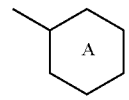

in a compound of formula IA or IB may be positively charged, e.g. in the form of a $NH_3^+$, $NH_2R_5^+$, $NH_2R_6^+$ or $NR_5R_6R_7^+$ group, wherein $R_5$ and $R_6$ are as defined above, with the exception of hydrogen, preferably $R_5$ and $R_6$ are $(C_{1-4})$alkyl; and $R_7$ is $(C_{1-4})$alkyl, e.g. methyl, more preferably $R_5$, $R_6$ and $R_7$ are methyl; with a negatively charged counterion, e.g. selected from counterions as conventional, such as hydroxy, halogen, e.g. chloride. A compound of the present invention in the form of a salt includes a compound of the present invention in the form of a salt with an acid, a salt with an an amine, a metal salt, a salt with more than one acid, e.g. in the form of a hydrochloride and additionally in the form of an hydroiodide, and a salt with an acid and additionally in the form of an amine salt, e.g. a tri$(C_{1-4})$alkylammonium salt, such as a trimethylammonium salt and additionally a hydrochloride, preferably a salt with one or two acids, a salt with an amine, or a salt with an amine and additionally with an acid.

In another aspect the present invention provides a a compound of the present invention in the form of a salt, which is a compound of formula $I_{SALT}$, including a compound of formula

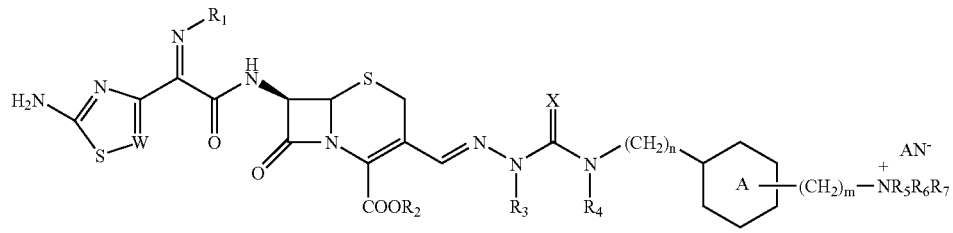

IA$_{SALT}$ or of formula

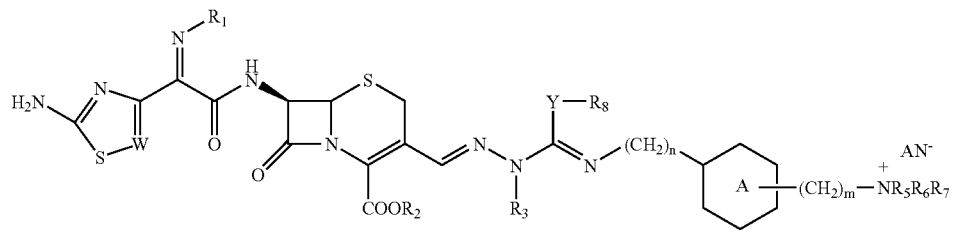

IB$_{SALT}$ wherein

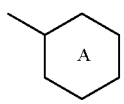

W, $R_1$, $R_2$, $R_3$, $R_4$, $R_5$, $R_6$, $R_8$, X, Y, m and n are as defined above, $R_7$ is $(C_{1-4})$alkyl, e.g. methyl, and $AN^-$ is a negatively charged counterion, e.g. selected from counterions as conventional, such as hydroxy, halogenide, e.g. chloride.

Preferably a compound of formula $I_{SALT}$ is a compound of $IA_{SALT}$.

In a compound of formula $Ia_{SALT}$, e.g. a compound of formula $IA_{SALT}$, preferably W is N, $R_1$ is halo$(C_{1-6})$alkoxy, e.g. —OCH$_2$F, $R_2$ and $R_4$ are hydrogen, $R_3$ is hydrogen or $(C_{1-4})$alkyl, e.g. methyl,

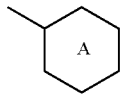

is cyclohexyl, $R_5$, $R_6$ and $R_7$ independently of each other are $(C_{1-4})$alkyl, e.g. methyl, X is NH or N—$(C_{1-4})$alkyl, n and m are 0, and $AN^-$ is halogenide, e.g. chloride.

A compound of the present invention in free form may be converted into a corresponding compound in the form of a salt; and vice versa.

A compound of the present Invention may exist in the form of isomers and mixtures thereof; e.g. optical isomers, diastereoisomers, cis/trans conformers, geometrical isomers. A compound of the present invention may e.g. contain asymmetric carbon atoms and may thus exist in the form of enantiomers or diastereoisomers and mixtures thereof, e.g. racemates. Any asymmetric carbon atom may be present in the (R)-, (S)- or (R,S)-configuration, preferably in the (R)- or (S)-configuration.

For example, the group $R_1$ attached to the imino group in a compound of formula I may be in the syn (Z) or anti (E) configuration and is preferably in the syn configuration. E.g., if

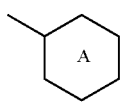

is cyclohexyl, the groups —NR$_4$— and —(CH$_2$)$_m$—NR$_5$R$_6$— attached to it may be in cis or in trans configuration.

Isomeric mixtures may be separated as appropriate, e.g. according, e.g. analogously, to a method as conventional, to obtain pure isomers. The present invention includes a compound of the present invention in any isomeric form and in any isomeric mixture.

The present invention also includes tautomers of a compound of formula I, where tautomers can exist. E.g. the group

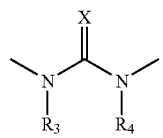

in a compound of formula IA, wherein $R_3$ and/or $R_4$ is/are hydrogen is in a chemical equilibrium with one of the following groups, depending on the meaning of $R_3$ and $R_4$:

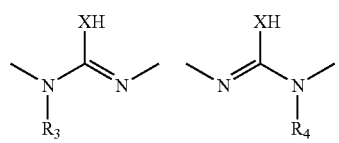

The present invention includes a compound of the present invention in any tautomeric form.

Any compound mentioned herein, e.g. a compound of the present invention, may be prepared as appropriate, e.g. according, such as analogously, to a method as conventional or as disclosed herein.

In another aspect the present invention provides a process for the production of a compound of formula IA or IB comprising reacting a compound of formula

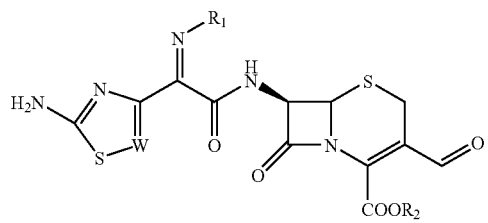

III wherein $R_1$, $R_2$ and W are as defined above, with a compound of formula

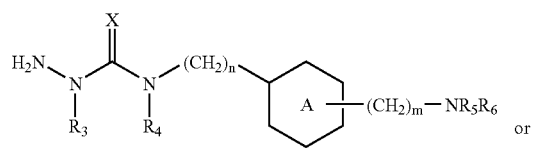

IVA or

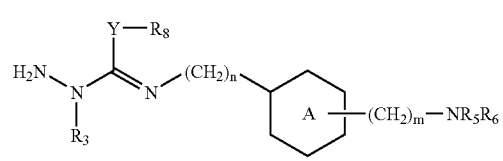

IVB wherein

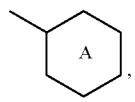

X, Y, R$_3$, R$_4$, R$_5$, R$_6$, R$_8$, n and m are as defined above, and isolating a compound of formula IA or IB obtained from the reaction mixture.

In an intermediate of formula III or of formula IVA or IVB (starting materials), functional groups, if present, optionally may be in protected form or in the form of a salt, if a salt-forming group is present. Protecting groups, optionally present, may be removed at an appropriate stage, e.g. according, e.g. analogously, to a method as conventional.

In another aspect the present invention provides an intermediate in the production of a compound of formula IA or IB, which intermediate is a compound of formula IVA or IVB as defined above.

Compounds of formula IVA or IVB are designated herein as "Intermediates of (according to) the present invention". The intermediates of the present invention, e.g. such as specified and obtained according to the Examples (Examples A to N), are useful in the production of compounds of formula IA and IB. Intermediates of formula IVA or IVB include intermediates in free base form, e.g. and in the form of a salt and/or optionally in the form of a solvent or in the form of a salt and a solvent, preferably in the form of a salt.

A compound of formula IA or IB thus obtained may be converted into another compound of formula IA or IB, respectively, e.g. a compound of formula IA or IB wherein R$_2$ is hydrogen may be converted into a compound of formula IA or IB wherein R$_2$ is an ester moiety, e.g. or a compound of formula IA or IB obtained in free form may be converted into a salt of a compound of formula IA or IB and vice versa. A compound of formula IA or IB may be isolated from the reaction mixture as appropriate, e.g. analogously to a method as conventional.

The above reaction is a condensation reaction of N-containing nucleophils to a carbonyl and may be carried out as appropriate, e.g. according, e.g. analogously to a method as conventional.

Intermediates (starting materials) of formula III and of formula IVA or IVB are known or may be prepared as appropriate, e.g. analogously, to a method as conventional or as specified.

Any compound described herein, e.g. a compound of the present invention and intermediates of formulae III, IVA and IVB may be prepared as appropriate, e.g. according, e.g. analogously, to a method as conventional, e.g. or as specified herein.

The compounds of the present invention, e.g. including a compound of formula IA or IB, exhibit pharmacological activity, e.g. beside low toxicity, and are therefore useful as pharmaceuticals. E.g., the compounds of the present invention exhibit antimicrobial, e.g. antibacterial, activity against e.g. gram negative and gram positive, bacteria, e.g. gram negative bacteria, such as *Escherichia*, e.g. *Escherichia coli; Enterobacter*, e.g. *Enterobacter cloacae* and *Enterobacter faecalis; Enterococcus*, e.g. *Enterococcus faecalis; Kiebsiella*, e.g. *Kiebsiella pneumoniae* and *Kiebsiella edwardii; Streptococcus*, e.g. *Streptococcus pneumoniae* and *Streptococcus pyogenes*; and *Pseudomonas*, e.g. *Pseudomonas aeruginosa*, e.g. and gram positive bactria, such as *Staphylococcus*, e.g. *Staphylococcus aureus*;

in vitro in the Agar Dilution Test according to National Commitee for Clinical Laboratory Standards (NCCLS) 1993, Document M7-A3 Vol.13, No. 25: "Methods for dilution Antimicrobial Susceptibility Tests for Bacteria that Grow Aerobically—Third Edition, Approved Standard"; and Document M11-A3 for anaerobic bacteria, in a concentration from about 0.001 to ca. 50 μm/ml (MIC) e.g. using strains including *Staphylococcus aureus* (ATCC 29213 and ATCC 9144); *Enterococcus faecalis* (ATCC 29212); *Haemophilus influenza* (NTCC 49247 and NCTC 11931); *Escherichia coli* (ATCC 25922 and ATCC 35218); *Klebsiella pneumoniae* (ATCC 11228); *Klebsielia edwardsii* (ATCC 10896); and in vivo in the septicaemia mouse model, in accordance to the method description Nr. 159 A-5, approved by Austrian Health Authorities (MA 58, no. 2968/95 of 12-Oct-1995), e.g. when administered at dosages from about 0.05 to 50 mg/kg body weight, such as ED$_{50}$ values of about 0.1 to 50 mg/kg body weight. E.g., in that model mice are infected with an ED 95% of *Staphylococcus aureus* (ATCC 4995), *Streptococcus pyogenes* (ATCC 29218), *Escherichia coli* and are treated 1 and 4 hours after infection. The EDSO values after subcutaneous administration with a compound of the present invention are calculated by Probit analysis of the administered dosages of compounds. Activity is determined by numbers of surviving animals per group of 8 mice per dosage unit day 5 after infection. ED$_{50}$ values of compounds of the present invention ranging form ca. 0.2 to 50 mg/kg body weight are obtained.

The compounds of the invention show an surprising overall activity spectrum. It has, for example, been determined that the MIC (μg/ml) of the compound of Example 1 against, for example Staphylococcus aureus (MSSA) is of ca. 0.05 to 0.2; against *Streptococcus pneumoniae* is about 0.0125; against *Klebsiella* is of 0.0125 to 0.8. Surprisingly the compound of Example 1 also shows activtiy against *Pseudomonas aeruginosa*.

In another aspect the present invention provides a compound of the present invention for use as a pharmaceutical, preferably as an antimicrobial agent, such as an antibiotic.

In another aspect the present invention provides the use of a compound of the present invention for the manufacture of a medicament, e.g. a pharmaceutical composition, for the treatment of a microbial diseases, for example diseases mediated by bacterias, such as *Escherichia, Enterobacter, Enterococcus, Klebsiella, Streptococcus, Staphylococcus* and *Pseudomonas*.

For pharmaceutical use a compound of the present invention includes one or more, preferably one, compounds of the present invention, e.g. a combination of two or more compounds of the present invention.

The compound of example 1 is a preferred compound of the present invention. It has, for example been determined that the MIC (μg/ml) of the compound of Example 1 against, for example *Klebsiella pneumoniae* is of about 0.0125. It is therefore, indicated that for the treatment of microbial diseases, e.g. bacterial diseases, the compounds of the present invention may be administered to larger mammals, for example humans, by similar modes of administration at similar dosages than conventionally used with cefotaxim.

In a further aspect the present invention provides a method of treatment of microbial diseases, e.g. which are mediated by bacteria, e.g. diseases mediated by bacterias, such as *Escherichia, Enterobacter, Enterococcus, Klebsiella, Streptococcus, Staphylococcus* and *Pseudomonas*, which treatment comprises administering to a subject in need of such treatment an effective amount of a compound of the present invention; e.g. in the form of a pharmaceutical composition.

Treatment includes treatment and prophylaxis.

The compounds of the present invention may be administered in the form of a pharmaceutically acceptable salt, e.g. an acid addition salt or metal salt; or in free form; optionally in the form of a solvate. The compounds of the present invention in the form of a salt exhibit the same order of activity as the compounds of the present invention in free form; optionally in the form of a solvate.

For such treatment, the appropriate dosage will, of course, vary depending upon, for example, the chemical nature and the pharmacokinetic data of a compound of the present invention employed, the individual host, the mode of administration and the nature and severity of the conditions being treated. However, in general, for satisfactory results in larger mammals, for example humans, an indicated daily dosage is in the range from about 0.1 g to about 2.0 g, of a compound of the present invention; conveniently administered, for example, in divided doses up to four times a day.

A compound of the present invention may be administered by any conventional route, for example enterally, e.g. including nasal, buccal, rectal, oral, administration; parenterally, e.g. including intravenous, intramuscular, subcutanous administration; or topically; e.g. including epicutaneous, intranasal, intratracheal administration; e.g. in form of coated or uncoated tablets, capsules, injectable solutions or suspensions, e.g. in the form of ampoules, vials, in the form of creams, gels, pastes, inhaler powder, foams, tinctures, lip sticks, drops, sprays, or in the form of suppositories.

The compounds of the present invention may be administered in the form of a pharmaceutically acceptable salt, e.g. an acid addition salt, amine or metal salt; or in free form; optionally in the form of a solvate.

A compound of the present invention may be used for pharmaceutical treatment according to the present invention alone, or in combination with one or more other pharmaceutically active agents. Such other agents include e.g. other antibiotics.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention In association with at least one pharmaceutical excipient, e.g. appropriate carrier and/or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers, e.g. further comprising another pharmaceutically active agent.

Such compositions may be manufactured according, e.g. analogously to a method as conventional, e.g. by mixing, granulating, coating, dissolving or lyophilizing processes. Unit dosage forms may contain, for example, from about 0.5 mg to about 2000 mg, such as 1 mg to about 500 mg.

In another aspect the present invention provides a compound of formula

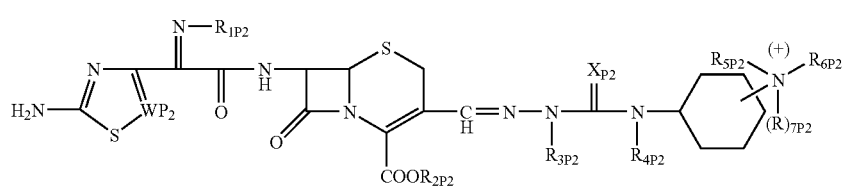

$I_{P2}$ wherein
$W_{P2}$ is CH or N,
$R_{1P2}$ is hydrogen, hydroxy, $(C_{1-6})$alkoxy, halo$(C_{1-6})$alkoxy, hydroxycarbonyl$(C_{1-6})$alkoxy or $(C_{1-6})$alkyloxycarbonyl$(C_{1-6})$alkoxy,
$R_{2P2}$ is hydrogen or an ester moiety,
$R_{3P2}$ is hydrogen, $(C_{1-6})$alkyl, allyl or cyclo$(C_{1-6})$alkyl,
$R_{4P2}$ is hydrogen or methyl,
$R_{5P2}$, $R_{6P2}$ and $R_{7P2}$ are independently from each other hydrogen, $(C_{1-6})$alkyl, $(C_{1-6})$alkylcarbonyl, arylcarbonyl, aryl$(C_{1-6})$alkycarbonyl, heteroaryl$(C_{1-6})$alkylcarbonyl, $(C_{1-6})$alkylsulfonyl, arylsulfonyl or aryl$(C_{1-6})$alkylsulfonyl, or $R_{7P2}$ is missing, and $N^+$—$R_{5P2}R_{6P2}R_{7P2}$ or N—$R_{5P2}R_{6P2}$ can be in o, m or p position, and
$X_{P2}$ is N—$R_{8P2}$, O, S, O—$R_{8P2}$ or S—$R_{8P2}$ wherein $R_{8P2}$ is hydrogen, $(C_{1-6})$alkyl, cyclo$(C_{1-6})$alkyl or aminocyclo$(C_{1-6})$alkyl.

In another aspect the present invention provides a compound of formula

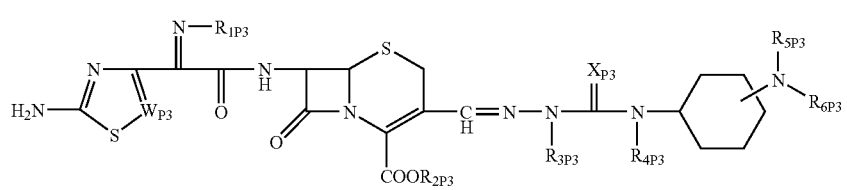

$I_{P3}$ wherein
$W_{P3}$ is CH or N,
$R_{1P3}$ is hydrogen, hydroxy, $(C_{1-6})$alkoxy, halo$(C_{1-6})$alkoxy, hydroxycarbonyl$(C_{1-6})$alkoxy or $(C_{1-6})$alkyloxycarbonyl$(C_{1-6})$alkoxy,
$R_{2P3}$ is hydrogen or an ester moiety, $R_{3P3}$ is hydrogen, $(C_{1-6})$alkyl, allyl or cyclo$(C_{3-8})$alkyl,
$R_{4P3}$ is hydrogen or methyl,
$R_{5P3}$ and $R_{6P3}$ independently from each other are hydrogen, $(C_{1-6})$alkyl, $(C_{1-6})$alkylcarbonyl, arylcarbonyl, aryl$(C_{1-6})$alkycarbonyl, heteroaryl$(C_{1-6})$alkylcarbonyl, $(C_{1-6})$alkylsulfonyl, arylsulfonyl or aryl$(C_{1-6})$alkylsulfonyl, and
$X_{P3}$ is N—$R_{8P3}$, O, S, O—$R_{8P3}$ or S—$R_{8P3}$ wherein $R_{8P3}$ is hydrogen, $(C_{1-6})$alkyl, cyclo$(C_{3-8})$alkyl or aminocyclo$(C_{3-8})$alkyl.

In another aspect the present invention provides a compound of formula

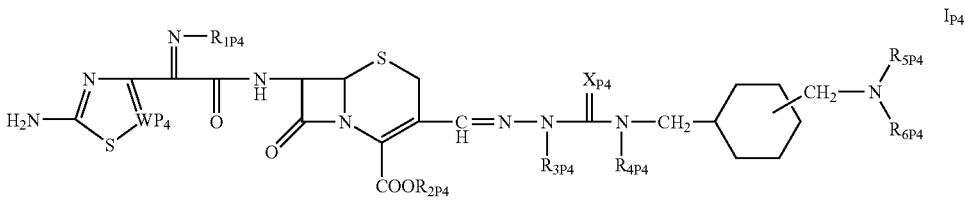

wherein
$W_{P4}$ is CH or N,
$R_{1P4}$ is hydrogen or O—$R_{1P4}$,
$R_{1P4}$ is hydrogen, $(C_{1-6})$alkyl, halo$(C_{1-6})$alkyl or hydroxycarbonyl$(C_{1-6})$alkyl,
$R_{2P4}$ is hydrogen or an ester moiety,
$R_{3P4}$ is hydrogen, $(C_{1-2})$alkyl, allyl or $(C_{3-8})$cycloalkyl,
$R_{4P4}$ is hydrogen or $(C_{1-2})$alkyl,
$R_{5P4}$ and $R_{6P4}$ independently of each other are hydrogen, $(C_{1-6})$alkyl, $(C_{1-6})$alkyl-carbonyloxy, arylcarbonyloxy, $(C_{1-6})$alkylsulfonyl, arylsulfonyl,
$X_{P4}$ is NH, oxygen or sulfur, and the $CH_2NR_{5P4}R_{6P4}$ group can be in o, m or p position.

In another aspect the present invention provides a compound of formula wherein $W_{P5}$ is CH or N, $R_{1P5}$ is hydrogen or O—$R_{1P5}$ $R_{1P5}$ is hydrogen, $(C_{1-6})$alkyl, halo$(C_{1-6})$alkyl or hydroxycarbonyl$(C_{1-6})$alkyl, $R_{2P5}$ is hydrogen or an ester moiety, $R_{3P5}$ is hydrogen, $(C_{1-2})$alkyl, allyl or $(C_{3-8})$cycloalkyl, $R_{4P5}$ is hydrogen or $(C_{1-2})$alkyl, $R_{5P5}$ and $R_{6P5}$ independently of each other are hydrogen, $(C_{1-6})$alkyl, $(C_{1-6})$alkyl-carbonyloxy, arylcarbonyloxy, $(C_{1-6})$alkylsulfonyl or arylsulfonyl, and $X_{P5}$ is NH, O or S.

In another aspect the present invention provides a compound of formula

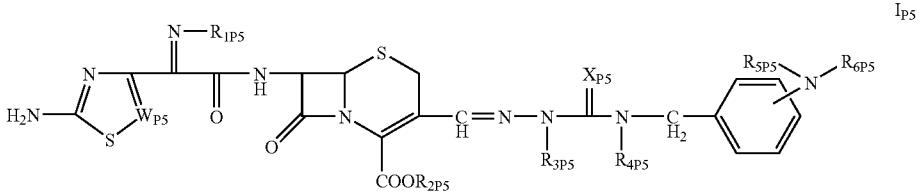

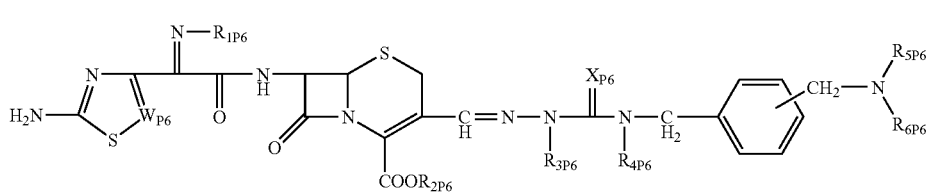

wherein
$W_{P6}$ is CH or N,
$R_{1P6}$ is hydrogen or O—$R_{1P6}$
$R_{1P6}$ is hydrogen, $(C_{1-6})$alkyl, halo$(C_{1-6})$alkyl or hydroxycarbonyl$(C_{1-6})$alkyl,
$R_{2P6}$ is hydrogen or an ester moiety,
$R_{3P6}$ is hydrogen, $(C_{1-2})$alkyl, allyl or $(C_{3-8})$cycloalkyl,
$R_{4P6}$ is hydrogen or $(C_{1-2})$alkyl,
$R_{5P6}$ and $R_{6P6}$ independently of each other are hydrogen, $(C_{1-6})$alkyl, $(C_{1-6})$alkyl-carbonyloxy, arylcarbonyloxy, $(C_{1-6})$alkylsulfonyl or arylsulfonyl, and
$X_{P6}$ is NH, O or S.

In the following examples all temperatures are in degrees Celsius (° C) and are uncorrected. $^1$H-NMR are detremined at 200 MHz and in DMSO-$d_6$, unless given otherwise.

The following abbreviations are used:

| AcCN | acetonitrile | EX | Example |
|------|--------------|-----|---------|
| BOC | tert•butoxycarbonyl | MeOH | methanol |
| DMA | N,N-dimethylacetamide | RT | room temperature |
| EtAc | ethyl acetate | TFA | trifluoracetic acid |
| EtOH | ethanol | | |

EXAMPLE 1

3-{(E)[[1-trans-(4-Amino-cyclohexylamino)-iminomethyl]-methylhydrazono]methyl}-7- {[(5-amino-1,2,4-thiadiazol-3-yl)-(Z)-(fluoromethoxyimino)-acetyl]amino}-3-cephem-4-carboxylic acid a) Benzylidene Derivative of 3-amino-1-(trans-4-aminocyclohexyl)-3-methyl-quanidine 35 g of the benzylidene derivative of S-methyl-2-methyl-isothlosemicarbazide in the form of a hydrochloride and 32.79 g of trans-1,4-diaminocyclohexane in 300 ml of MeOH are refluxed. The mixture obtained is stirred at RT, a precipitate formed is filtered off and solvent is evaporated. The evaporation residue obtained is treated with 217.5 ml of 2M HCl, a precipitate formed is filtered off, washed and dried. The volume of the filtrate obtained is brought to about 150 ml, a precipitate is formed is filtered off, washed and dried. The dried, combined precipitates are recristallized from $H_2O$ and the benzylidene derivative of 3-amino-1-(trans-4-aminocyclo hexyl)-3-methyl-guanidine in the form of a monohydrochloride is obtained.

b) 3-Amino-1-(trans-4-aminocyclohexyl)-3-methyl-quanidine

From a mixture of 24.74 g of benzylidene derivative of 3-amino-1-(trans4-aminocyclohexyl)-3-methyl-guanidine in the form of a monohydrochloride in 79.9 ml of 2M HCl, benzaldehyde is destilled off and solvent from the remaining mixture is evaporated. 3-Amino-1-(trans-4-aminocyclohexyl)-3-methyl-guanidine in the form of a dihydrochloride is obtained.

c) 3-{(E)[[1-trans-(4-amino-cyclohexylamino)-iminomethyl]-methylhydrazono]methyl}-7-{[5-amino-[1,2,4]thiadiazol-3-yl)-(Z)-(fluoromethoxyimino)-acetyl]amino}-3-cephem-4-carboxylic acid 2.78 g of N-(1,4,5a,6-tetrahydro-3-hydroxy-1,7-dioxo-3H,7H-azeto(2,1-b)furo(3,4-d)(1,3)-thiazin-6yl)-2-(5-amino-1,2,4-thiadiazol-3-yl)-(Z)-2-(fluoromethoxyimino) acetic acid amide are added to a mixture of 2 g of 3-amino-1-(trans-4-aminocyclohexyl)-3-methyl-guanidine in the form of a dihydrochloride in 3.4 ml of 2M HCl and 6.1 ml of DMA and the suspension obtained is stirred at RT. The mixture obtained is poured into AcCN under stirring. A precipitate formed is filtrated off, washed and dried. 3-{(E)[[1-trans-(4-Amino-cyclohexylamino)-iminomethyl]-methylhydrazono]methyl}-7-{[(5-amino-1,2,4-thiadiazol-3-yl)-(Z)-(fluoromethoxyimino)-acetyl] amino}-cephem-4-carboxylic acid in the form of a trihydrochloride is obtained.

d) 3-{(E)[[1-trans-(4-Amino-cyclohexylamino)-iminomethyl]-methylhydrazono]methyl}-7-{[-(5-amino-1,2,4-thiadiazol-3-yl)-(Z)-(fluoromethoxyimino)-acetyl]amino}-3-cephem-4-carboxylic acid 10 g of crude 3-{(E)[[1-trans-(4-amino-cylohexylamino)-iminomethyl]-methylhydrazono]methyl}-7-{[5-amino-1,2,4-thiadiazol-3-yl)-(Z)-(fluoromethoxyimino)-acetyl] amino}-3-cephem-4-carboxylic acid in the form of a trihydrochloride are dissolved in 42 ml of $H_2O$ and subjected to chromatography (LiChroprep RP$^{18}$, Merck, grain size 40-63 μm). Fractions containing the desired product in the form of a monohydrochloride are combined and optionally lyophilised. 3-{(E)[[1-Trans-(4-amino-cyclohexylamino)-iminomethyl]-methylhydrazono]methyl}-7-{[(5-amino-1,2,4-thiadiazol-3-yl)-(Z)-(fluoromethoxyimino)-acetyl] amino}-3-cephem-4-carboxylic acid in the form of a hydrochloride is obtained.

$^1$H-NMR: 1.30-1.70, m, 4H, $CCH_2$; 1.80-2.10, m, 4H, $CCH_2$; 2.88-3.10, m, 1H, NCH; 3.32, s, 3H, $NCH_3$; 3.42-3.70, m, 2H, 1H from $SCH_2$ and 1H from NCH; 4.25, part of the AB-quartet, J=18 Hz, 1H, $SCH_2$; 5.28, d, J=5 Hz, 1H, β-lactam; 5.79, d, J=55 Hz, 2H, $CH_2F$; 5.75, dd, J=5 Hz and 8 Hz, 1H, β-lactam; 8.10, s, 1H, CH=N; 9.84, d, J=8 Hz, 1H, NH.

Analogously to the method as described in Example 1c) and 1d) (purification by chromatograpy is carried out optionally), but using appropriate starting materials (intermediates), compounds of formula

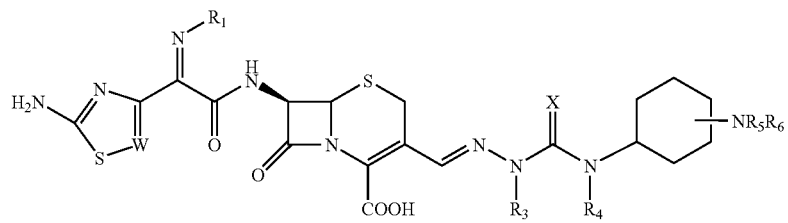

wherein X, W, $R_1$, $R_3$, $R_4$, $R_5$, $R_6$ and $R_7$ are as defined in TABLE 1 below, are obtained. "P" in TABLE 1 indicates the position of the —$NR_5R_6$ group in the cyclohexyl ring (o=ortho, m=meta and p=para). $R_7$ is only present where the compound is in the form of an ammonium salt. In the compounds of examples 2, 20, 22, 27, 30 and 32, the group —$NR_4$— and the group N—$R_5R_6$ attached to the cyclohexyl ring are in the cis configuration, in all other examples in the trans configuration. Compounds of EX 1 to 43 are obtained in the form of a hydrochloride and EX 10, 12 and 17 additionally in the form of a trimethylammonium chloride, i.e. the group $NR_5R_6$ is a group $N^+R_5R_6R_7$ $Cl^-$.

TABLE 1

| EX | W | $R_1$ | $R_3$ | $R_4$ | $R_5$ | $R_6$ | X | P |
|---|---|---|---|---|---|---|---|---|
| 1 | N | —$OCH_2F$ | $CH_3$ | H | H | H | NH | p |
| 2 | N | —$OCH_2F$ | $CH_3$ | H | H | H | NH | p |
| 3 | N | —$OCH_2F$ | ethyl | H | H | H | NH | p |
| 4 | CH | OH | $CH_3$ | H | H | H | NH | p |
| 5 | CH | $OCH_3$ | $CH_3$ | H | H | H | NH | p |
| 6 | N | —$OCH_2F$ | allyl | H | H | H | NH | p |
| 7 | N | —$OCH_2F$ | H | H | H | H | NH | o |
| 8 | N | —$OCH_2F$ | H | H | H | H | NH | p |
| 9 | N | —$OCH_2F$ | H | H | $CH_3$ | $CH_3$ | NH | p |
| 10 | N | —$OCH_2F$ | H | H | $CH_3$ | $CH_3$ | NH | p |
| 11 | N | —$OCH_2F$ | H | H | H | H | N—$CH_3$ | o |
| 12 | N | —$OCH_2F$ | $CH_3$ | H | $CH_3$ | $CH_3$ | NH | p |
| 13 | N | —$OCH_2F$ | $CH_3$ | H | [4-aminophenylsulfonyl] | H | NH | p |
| 14 | N | —$OCH_2F$ | H | $CH_3$ | $CH_3$ | H | N—$CH_3$ | p |
| 15 | N | —$OCH_2F$ | H | H | H | H | N—$CH_3$ | p |
| 16 | N | —$OCH_2F$ | H | H | $CH_3$ | $CH_3$ | N—$CH_3$ | p |
| 17 | N | —$OCH_2F$ | H | H | $CH_3$ | $CH_3$ | N—$CH_3$ | p |
| 18 | N | —$OCH_2F$ | H | H | H | H | N—$CH_3$ | o |
| 19 | N | —$OCH_2F$ | $CH_3$ | H | H | H | [4-iminocyclohexylamine] | p |
| 20 | N | —$OCH_2F$ | $CH_3$ | H | H | H | NH | m |
| 21 | N | —$OCH_2F$ | $CH_3$ | H | H | H | NH | m |
| 22 | N | —$OCH_2F$ | $CH_3$ | H | H | H | NH | m |
| 23 | N | —$OCH_2F$ | $CH_3$ | H | H | H | NH | m |
| 24 | CH | —$OC(CH_3)_2(COOH)$ | $CH_3$ | H | H | H | NH | p |
| 25 | N | —$OCH_2F$ | $CH_3$ | H | H | H | S | p |
| 26 | N | —$OCH_2F$ | $CH_3$ | H | H | H | O | p |
| 27 | N | —$OCH_2F$ | $CH_3$ | H | H | H | NH | m |
| 28 | N | —$OCH_2F$ | $CH_3$ | H | H | H | N—$CH_3$ | p |

TABLE 1-continued

| EX | W | R$_1$ | R$_3$ | R$_4$ | R$_5$ | R$_6$ | X | P |
|----|---|-------|-------|-------|-------|-------|---|---|
| 29 | N | —OCH$_2$F | cyclopropyl | H | H | H | NH | p |
| 30 | N | —OCH$_2$F | H | CH$_3$ | H | H | N—CH$_3$ | p |
| 31 | N | —OCH$_2$F | H | CH$_3$ | H | H | N—CH$_3$ | p |
| 32 | N | —OCH$_2$F | CH$_3$ | CH$_3$ | H | H | N—CH$_3$ | p |
| 33 | N | —OCH$_2$F | CH$_3$ | H | allyl | H | NH | p |
| 34 | N | —OCH$_2$F | CH$_3$ | H | allyl | allyl | NH | p |
| 35 | N | —OCH$_2$F | CH$_3$ | H | i-propyl | H | i-propyl-imino | p |
| 36 | N | —OCH$_2$F | CH$_3$ | H | i-propyl | H | NH | p |
| 37 | N | —OCH$_2$F | CH$_3$ | H | ethyl | H | NH | p |
| 38 | N | —OCH$_2$F | CH$_3$ | H | ethyl | ethyl | NH | p |
| 39 | N | —OCH$_2$F | CH$_3$ | H | n-propyl | H | NH | p |
| 40 | N | —OCH$_2$F | CH$_3$ | H | n-propyl | n-propyl | NH | p |
| 41 | N | —OCH$_2$F | CH$_3$ | H | CH$_3$ | H | NH | p |
| 42 | N | —OCH$_2$F | H | CH$_3$ | H | H | NH | p |
| 43 | N | —OCH$_2$F | CH$_3$ | CH$_3$ | H | H | NH | p |

EXAMPLE 44

3-{(E)[[1-trans-(4-Acetylamino-cyclohexylamino)-iminomethyl]-methylhydrazono]methyl}-7-{[(5-amino-1,2,4-thiadiazol-3-yl)-(Z)-(fluoromethoxyimino)-acetyl]amino}-3-cephem-4-carboxylic acid 0.6395 g of N,O-bis-(trimethylsilyl)-acetamid are added to suspension of 0.2579 g of 3-{(E)[[1-trans-(4-amino-cyclohexylamino)-iminomethyl]-methylhydrazono]methyl}-7-{[(5-amino-1,2,4-thiadiazol-3-yl)-(Z)-(fluoromethoxyimino)-acetyl]amino}-3-cephem-4-carboxylic acid in the form of a trihydrochloride in 20 ml of AcCN. To the solution obtained 0.026 ml of acetylchloride are added, the mixture obtained is stirred and treated with 0.115 ml of H$_2$O. A precipitate is formed, filtrated off and dried. 3-{(E)[[1-trans-(4-Acetylamino-cyclohexylamino)-iminomethyl]-methylhydrazono]methyl}-7-{2-(5-amino-[1,2,4]thiadiazol-3-yl)-2-[(Z)-fluoromethoxyimino]-acetylamino}cephem-4-carboxylic acid in the form of a dihydrochloride is obtained.
$^1$H-NMR: 1.10-1.68, m, 4H, CCH$_2$; 1.72-2.00, m, 7H, 4H from CCH$_2$ and 3H from CH$_3$; 3.32, s, 3H, NCH$_3$; 3.40-3.70, m, 3H, 2H from NCH and 1H from SCH$_2$; 4.56, part of the AB-quartet, J=18 Hz, 1H, SCH$_2$; 5.27, d, J=5 Hz, 1H, β-lactam; 5.78, d, J=55 Hz, 2H, CH$_2$F; 5.94, dd, J=5 Hz and 8 Hz, 1H, β-lactam; 8.09, s, 1H, CH═N; 9.85, d, J=8 Hz, 1H, NH.

Analogously to the method as described in Example 44, but using appropriate starting materials (intermediates), compounds of formula

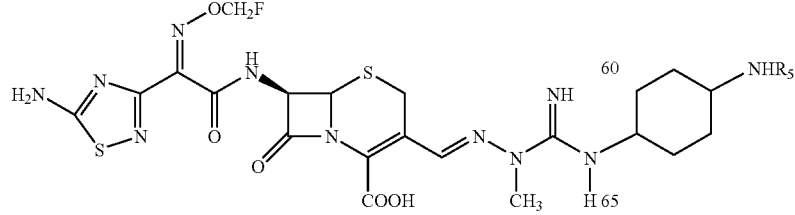

wherein R₅ is as defined in TABLE 2 below. ¹H-NMR characterisation data of the compounds of examples 45 to 49 are also indicated in TABLE 2. Compounds of EX 45 to 49 are obtained in the form of a hydrochloride.

5a,6-tetrahydro-3-hydroxy-1,7-dioxo-3 H,7 H-azeto(2,1-b) furo(3,4-d)(1,3)-thiazin-6-yl)-2-(5-amino-1,2,4-thiadiazol-3-yl)-(Z)-2-(fluoromethoxyimino) acetic acid amide in 0.5 ml of DMA, the mixture obtained is stirred and 0.165 ml of

TABLE 2

| EX | R₅ | ¹H-NMR |
|---|---|---|
| 45 | acetylphenyl group | 1.32-1.72, m, 4H, CCH₂; 1.80-2.12, m, 4H, CCH₂; 3.33, s, 3H, NCH₃; 3.40-3.90, m, 3H, 2H from NCH and 1H from SCH₂; 4.59, part of the AB-quartet, J=18 Hz, 1H, SCH₂; 5.28, d, J=5 Hz, 1H, β-lactam; 5.79, d, J=55 Hz, 2H, CH₂F; 5.95, dd, J=5 Hz and 8 Hz, 1H, β-lactam; 7.32-7.58, m, 3H, aromatic-H; 7.70-7.90, m, 2H, aromatic-H; 8.10, s, 1H, CH=N; 9.86, d, J=8 Hz, 1H, NH |
| 46 | 2-acetoxyacetylphenyl group | 1.25-1.70, m, 4H, CCH₂; 1.75-2.08, m, 4H, CCH₂; 2.18, s, 3H, CH₃; 3.30, s, 3H, NCH₃; 3.48-3.80, m, 3H, 2H from NCH and 1H from SCH₂; 4.54, part of the AB-quartet, J=18 Hz, 1H, SCH₂; 5.28, d, J=5 Hz, 1H, β-lactam; 5.79, d, J=55 Hz, 2H, CH₂F; 5.96, dd, J=5 Hz and 8 Hz, 1H, β-lactam; 7.08-7.60, m, 4H, aromatic-H; 8.08, s, 1H, CH=N; 9.86, d, J=8 Hz, 1H, NH |
| 47 | phenoxyacetonyl group | 1.28-1.68, m, 4H, CCH₂; 1.75-2.02, m, 4H, CCH₂; 3.31, s, 3H, NCH₃; 3.48-3.75, m, 3H, 2H from NCH and 1H from SCH₂; 4.20, part of the AB-quartet, J=18 Hz, 1H, SCH₂; 4.50, s, 2H, NCH₂; 5.11, d, J=5 Hz, 1H, β-lactam; 5.66, dd, J=5 Hz and 8 Hz, 1H, β-lactam; 5.78, d, J=55 Hz, 2H, CH₂F; 6.82-7.02, m, 3H, aromatic-H; 7.22-7.40, m, 2H, aromatic-H; 8.08, s, 1H, CH=N; 9.75, d, J=8 Hz, 1H, NH |
| 48 | 4-(acetamido)phenylsulfonylmethyl group | 1.15-1.55, m, 4H, CCH₂; 1.58-1.90, m, 4H, CCH₂; 2.05, s, 3H, CH₃; 2.75-3.05, m, 1H, NCH; 3.25, s, 3H, NCH₃; 3.32-3.68, m, 2H, 1H from NCH and 1H from SCH₂; 4.50, part of the AB-quartet, J=18 Hz, 1H, SCH₂; 5.28, d, J=5 Hz, 1H, β-lactam; 5.77, d, J=55 Hz, 2H, CH₂F; 5.96, dd, J=5 Hz and 8 Hz, 1H, β-lactam; 7.65-7.90, m, 4H, aromatic-H; 8.05, s, 1H, CH=N; 9.84, d, J=8 Hz, 1H, NH |
| 49 | 2-thienylacetonyl group | 1.15-1.68, m, 4H, CCH₂; 1.72-2.05, m, 4H, CCH₂; 3.25-3.72, m, 8H, 3H from NCH₃, 2H from NCH, 2H from NCH₂ and 1H from SCH₂; 4.20, part of the AB-quartet, J=18 Hz, 1H, SCH₂; 5.12, d, J=5 Hz, 1H, β-lactam; 5.70, dd, J=5 Hz and 8 Hz, 1H, β-lactam; 5.76, d, J=55 Hz, 2H, CH₂F; 6.80-7.00, m, 2H, thiophenyl-H; 7.30-7.40, m, 1H, thiophenyl-H; 8.08, s, 1H, CH=N; 9.76, d, J=8 Hz, 1H, NH |

EXAMPLE 50

3-{(E)[[(trans-4-aminocyclohexylimino)methylthiomethyl]methylhydrazono]methyl}-7-{[(5-amino-1,2,4-thiadiazol-3-yl)-(Z)-(fluoromethoxylmino)-acetyl]amino}-3-cephem-4-carboxylic acid a) 3-{(E)[[trans-4-((1,1-dimethylethoxy)carbonyl)aminocyclohexylimino) methylthio-methyl]-methylhydrazono]methyl}-7-{[(5-amino-1,2,4-thiadiazol-3-yl)-(Z)-(fluoromethoxyimino)-acetyl]amino}-3-cephem-4-carboxylic acid A solution of 0.103 g of [trans-4-(3-amino-2,3-dimethylisothioureido)cyclohexyl]-carbamic acid tert-butyl ester in 2.5 ml of DMA are added to a solution of 0.144 g of N-(1,4, 2N HCl are added. The mixture obtained is stirred at RT, poured onto tert-butyl-methyl-ether and stirred at RT. A precipitate forms and is filtrated off, washed and dried. 3-{(E)[[trans-4-((1,1-Dimethylethoxy) carbonyl)amino-cyclohexylimino)methylthiomethyl]methylhydrazono]methyl}-7-{[(5-amino-1,2,4-thiadiazol-3-yl)-(Z)-(fluoromethoxyimino)-acetyl]amino}-3-cephem-4-carboxylic acid in the form of a hydrochloride is obtained.

b) 3-{(E)[[(trans-4-aminocyclohexylimino)methylthiomethyl]methylhydrazono]methyl}-7-{[(5-amino-1,2,4-thiadiazol-3-yl)-(Z)-(fluoromethoxyimino)-acetyl]amino}-3-cephem-4-carboxylic acid 2 ml of TFA are added to a cooled suspension of 0.235 g of 3-{(E)[[trans-4-((1,1-dimethylethoxy)carbonyl)amino-cyclohexylimino)methylthiomethyl]methylhydrazono]methyl}-7-{[(5-amino-1,2,4-thiadiazol-3-yl)-(Z)-(fluoromethoxyimino)-acetyl]amino}-3-cephem-4-carboxylic acid in the form of a hydrochloride in 2 ml of $CH_2Cl_2$ at 0° C. The solution obtained is stirred and solvent is evaporated. The evaporation residue obtained is treated with $H_2O$ and a precipitate formed is filtrated off. The filtrate obtained is lyophilzed and the lyophilisation residue obtained is treated with $H_2O$ and 2N HCl. The solution obtained is subjected to chromatography (LiChroprep $RP^{18}$) and fractions containing the desired compound are combined and lyophilised. 3-{(E)[[(trans-4-Aminocyclohexylimino)methyl-thiomethyl]methylhydrazono]-methyl}-7-{[(5-amino-1,2,4-thiadiazol-3-yl)-(Z)-(fluoromethoxyimino)-acetyl]amino}-3-cephem-4-carboxylic acid in the form of a hydrochloride is obtained. $^1$H-NMR: 1.30-1.78, m, 4H, $CCH_2$; 1.88-2.12, m, 4H, $CCH_2$; 2.64, s, 3H, $SCH_3$; 2.90-3.18, m, 1H, NCH; 3.52-3.72, m, 4H, 3H from $NCH_3$ and 1H from $SCH_2$; 3.88-4.12, m, 1H, NCH; 4.32, part of the AB-quartet, J=18 Hz, 1H, $SCH_2$; 5.30, d, J=5 Hz,1H, β-lactam; 5.77, d, J=55 Hz, 2H, $CH_2F$; 5.98, dd, J=5 Hz and 8 Hz,1H, β-lactam; 8.38, s, 1H, CH=N; 9.88, d, J=8 Hz, 1H, NH.

EXAMPLE 51

3-{(E)[[1-(3-{Aminomethyl}cyclohexylmethyl)-iminomethyl]-methylhydrazono]methyl}- 7-{[(5-amino-1,2,4-thiadiazol-3-yl)-(Z)-(fluoromethoxyimino)-acetyl]amino}-3-cephem-4- carboxylic acid (in the form of a hydrochloride)

is obtained according to the method as described in Example 1, but using the appropriate starting materials. $^1$H-NMR: 0.40-1.92, m, 10H, 8H from $CCH_2$ and 2H from CCH; 2.58-2.85, m, 2H, $NCH_2$; 3.05-3.28, m, 2H, $NCH_2$; 3.34, s, 3H, $NCH_3$; 3.50 and 4.59, AB-quartet, J=18 Hz, 2H, $SCH_2$; 5.28, d, J=5 Hz, 1H, β-lactam; 5.78, d, J=55 Hz, 2H, $CH_2F$; 5.95, dd, J=5 Hz and 8 Hz, 1H, β-lactam; 8.10, s, 1H, CH=N; 9.84, d, J=8 Hz, 1H, NH.

According to the method as described in Example 1, but using appropriate starting materials (intermediates), compounds of formula IA wherein W is N, $R_2$ is hydrogen, $R_3$ is methyl, $R_4$, $R_5$ and $R_6$ are hydrogen, n=1, m=1,

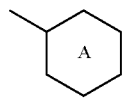

is cyclohexyl and $R_1$ is as described in TABLE 3 below, are obtained. "P" in TABLE 3 indicates the position of the $—CH_2)_m—NR_5R_6$ group in the cyclohexyl ring (m=meta and p=para). In the compound of example 52 the group $—NR_4—$ and the group $—CH_2)_m— NR_5R_6$ attached to the cyclohexyl ring are in the cis configuration, in all other examples in the trans configuration. $^1$H-NMR characterisation data of the compounds of examples 52 to 54 are also indicated in TABLE 3. Compounds of EX 52 to 54 are obtained in the form of a hydrochloride.

TABLE 3

| EX | $R_1$/P | $^1$H-NMR |
|---|---|---|
| 52 | $CH_2F$ m | 0.50-2.08, m, 8H from $CCH_2$; 2.55-2.90, m, 2H, $NCH_2$; 3.00-3.38, m, 2H, $NCH_2$; 3.34, s, 3H, $NCH_3$; 3.49 and 4.59, AB-quartet, J=18 Hz, 2H, $SCH_2$; 5.28, d, J=5 Hz, 1H, β-lactam; 5.77, d, J=55 Hz, 2H, $CH_2F$; 5.96, dd, J=5 Hz and 8 Hz, 1H, β-lactam; 8.10, s, 1H, CH=N; 9.84, d, J=8 Hz, 1H, NH |
| 53 | $CH_2F$ p | 0.70-1.10, m, 4H, $CCH_2$; 1.40-1.90, m, 6H, 4H from $CCH_2$ and 2H from CCH; 2.58-2.75, m, 2H, $NCH_2$; 3.10-3.30, m, 2H, $NCH_2$; 3.34, s, 3H, $NCH_3$; 3.50 and 4.60, AB-quartet, J=18 Hz, 2H, $SCH_2$; 5.28, d, J=5 Hz, 1H, β-lactam; 5.77, d, J=55 Hz, 2H, $CH_2F$; 5.94, dd, J=5 Hz and 8 Hz, 1H, β-lactam; 8.09, s, 1H, CH=N; 9.84, d, J=8 Hz, 1H, NH |
| 54 | OH p | 0.70-1.12, m, 4H, $CCH_2$; 1.40-1.92, m, 6H, 4H from $CCH_2$ and 2H from CCH; 2.56-2.78, m, 2H, $NCH_2$; 3.08-3.30, m, 2H, $NCH_2$; 3.34, s, 3H, $NCH_3$; 3.55 and 4.57, AB-quartet, J=18 Hz, 2H, $SCH_2$; 5.14, d, J=5 Hz, 1H, β-lactam; 5.72, dd, J=5 Hz and 8 Hz, 1H, β-lactam; 6.66, s, 1H, CH thiazol; 7.14. b, 2H, NH; 8.11, s, 1H, CH=N; 9.82, d, J=8 Hz, 1H, NH |

According to the method as described in Example 1, but using appropriate starting materials the compounds of Examples 55 to 58 are obtained:

EXAMPLE 55

3-{(E)[[1-(3-(aminobenzylamino)-iminomethyl]-methylhydrazono]-methyl}-7-{[(5-amino-1,2,4-thiadiazol-3-yl)-(Z)-(fluoromethoxyimino)-acetyl]-amino}-3-cephem-4-carboxylic acid (in the form of a hydrochloride)

$^1$H-NMR: 3.38, s, 3H, $NCH_3$; 3.52, part of the AB-quartet, J=18 Hz, 1H, $SCH_2$; 4.50-4.75, m, 3H, 2H from $NCH_2$ and 1H from $SCH_2$; 5.29, d, J=5 Hz, 1H, β-lactam; 5.76, d, J=55 Hz, 2H, $CH_2F$; 5.95, dd, J=5 Hz and 8 Hz, 1H, β-lacatm; 7.25-7.60, m, 4H, aromatic H; 8.17, s, 1H, CH=N; 9.75, d, J=8 Hz, 1H, NH

EXAMPLE 56

3-{(E)[[1-(3-(aminomethyl)benzylamino)-iminomethyl]-methylhydrazono]-methyl}-7-{[(5-amino-1,2,4-thiadiazol-3-yl)-(Z)-(fluoromethoxyimino)-acetyl]-amino}-3-cephem-4-carboxylic acid (in the form of a hydrochloride)

$^1$H-NMR: 3.41, s, 3H, $NCH_3$; 3.52, part of the AB-quartet, J=18 Hz, 1H, $SCH_2$; 3.88-4.12, m, 2H, $NCH_2$; 4.40-4.80, m, 3H, 2H from $NCH_2$ and 1H from $SCH_2$; 5.28, d, J=5 Hz,1H, β-lactam; 5.78, d, J=55 Hz, 2H, $CH_2F$; 5.96, dd, J=5 Hz and 8 Hz, 1H, β-lactam; 7.22-7.58, m, 4H, aromatic H; 8.14, s, 1H, CH=N; 9.84, d, J=8 Hz, 1H, NH

EXAMPLE 57

Compound of formula IA in the form of a hydrochloride wherein

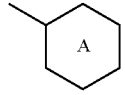

is phenyl, X is NH, $R_1$ is $OCH_2F$, $R_3$ is $CH_3$, $R_2$, $R_4$, $R_5$, $R_6$ are H, n=1, m=1 and the $—(CH_2)_m—NR_5R_6$ group in the phenyl ring is in the para position.

$^1$H-NMR: 3.38, s, 3H, $NCH_3$; 3.52, part of the AB-quartet, J=18 Hz,1H, $SCH_2$; 3.90-4.12, m, 2H, $NCH_2$; 4.50-4.80, m, 3H, 2H from $NCH_2$ and 1H from $SCH_2$; 5.28, d, J=5 Hz, 1H, β-lactam; 5.78, d, J=55 Hz, 2H, $CH_2F$; 5.96, dd, J=5 Hz and 8 Hz, 1H, β-lactam; 7.28-7.60, m, 4H, aromatic H; 8.14, s, 1H, CH=N; 9.84, d, J=8 Hz, 1H, NH.

EXAMPLE 58

Compound of formula IA in the form of a hydrochloride wherein

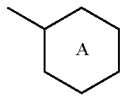

is phenyl, X is NH, $R_1$ is $OCH_2F$, $R_3$ is $CH_3$, $R_2$, $R_4$, $R_5$, $R_6$ are H, n=1, m=1 and the —$(CH_2)_m$—$NR_5R_6$ in the phenyl ring is in the para position.

$^1$H-NMR: 3.37, s, 3H, $NCH_3$; 3.57, part of the AB-quartet, J=18 Hz, 1H, $SCH_2$; 3.90-4.10, m, 2H, $NCH_2$; 4.45-4.75, m, 3H, 2H from $NCH_2$ and 1H from $SCH_2$; 5.15, d, J=5 Hz, 1H, β-lactam; 5.74, dd, J=5 Hz and 8 Hz, 1H, β-lactam; 6.88, s, 1H, CH thiazol; 7.20-7.55, m, 4H, aromatic H; 8.15, s, 1H, CH=N; 9.78, d, J=8 Hz, 1H, NH.

INTERMEDIATES

EXAMPLE A

3-Amino-1-(trans-4-aminocyclohexyl)-guanidine a) [trans-4-(3-Ethoxycarbonyl-thioureido)cyclohexyl]carbamic acid tert-butyl ester To a solution of 1.10 g of (4-amino-cyclohexyl)-carbamic acid tert-butyl ester in 25 ml of EtAc 0.58 ml of ethoxycarbonyl-isothiocyanat are added and the mixture obtained is stirred at RT. The precipitate formed is filtered and washed with diethylether. [trans-4-(3-Ethoxycarbonyl-thioureido)cyclohexyl]carbamic acid tert-butyl ester is obtained.

b) (trans-4-Thioureido-cyclohexyl)-carbamic acid tert-butyl ester 7.4 ml of 4M NaOH are added to a suspension of 1.69 g of [trans-4-(3-ethoxycarbonyl-thioureido)cyclohexyl]carbamic acid tert-butyl ester in 10 ml of $H_2O$ and 15 ml of EtOH. The mixture obtained is kept at 90° for 30 minutes at RT. The precipitate formed is filtered and washed with diethylether. (trans-4-Thioureido-cyclohexyl)-carbamic acid tert-butyl ester is obtained.

c) [trans-4-(2-Methyl-isothioureido)-cyclohexyl]-carbamic acid tert-butyl ester

A mixture of 1.19 g of (trans-4-thioureido-cyclohexyl)-carbamic acid tert-butyl ester and 0.41 ml of methyliodide in 50 ml of MeOH is stirred at RT. From the mixture obtained solvent is evaporated and [trans-4-(2-methyl-isothioureido)-cyclohexyl]-carbamic acid tert-butyl ester in the form of a hydrolodide is obtained.

d) [trans-4-(2-Methyl-isothioureido)-cyclohexyl]-carbamic acid tert-butyl ester 40 ml of a strong basic ion exchanger in chloride form (Amberlite IRA 400 (Cl)$^R$) are added to a suspension of 2.06 g of [trans-4-(2-methyl-isothioureido)-cyclohexyl]-carbamic acid tert-butyl ester in the form of a hydroiodide in 50 ml of $H_2O$. The mixture otained is stirred at RT, the ion exchanger is filtrated off and the filtrate obtained is lyophilised [trans-4-(2-Methyl-isothioureido)-cyclohexyl]-carbamic acid tert-butyl ester in the form of a hydrochloride is obtained.

e) [trans-4-((Hydrazino)iminomethyl)aminocyclohexyl]-carbamic acid tert-butyl ester 0.183 ml of hydrazine monohydrate are added to a solution of 1.11 g of [trans-4-(2-methyl-isothioureido)-cyclohexyl]-carbamic acid tert-butyl ester in 50 ml of EtOH, the mixture obtained is refluxed and solvent is evaporated. [trans-4-(Hydrazino)iminomethyl) aminocyclohexyl]-carbamic acid tert-butyl ester in the form of a hydrochloride is obtained.

f) 3-Amino-1-(trans-4-aminocyclohexyl)-quanidine

A mixture of 1.15 g of [trans-4-(hydrazino)iminomethyl)-aminocyclohexyl]-carbamic acid tert-butyl ester in the form of a hydrochloride and 4.2 ml of 5.4M HCl (in MeOH) in 50 ml of MeOH is stirred at RT. The volume of the mixture is reduced and a precipitate formed is filtrated off, washed and dried. 3-Amino-1-(trans-4-aminocyclohexyl)-guanidine in the form of a dihydrochloride is obtained. $^1$H-NMR: 1.10-1.60, m, 4H, $CCH_2$; 1.72-2.12, m, 4H, $CCH_2$; 2.75-3.08, m, 1H, NCH; 3.30-3.60, m, 1H, NCH; 8.30, b, 3H, NH.

According to the method as set out in Example A, but using appropriate starting materials, the compounds of Examples A2 to A4 of TABLE 4 below in the form of a hydrochloride are obtained. $^1$H-NMR data are also set out in TABLE 4.

TABLE 4

| EX | Compound of formula | $^1$H-NMR |
|---|---|---|
| A2 | | 1.08-2.20, m, 8H, $CCH_2$; 3.00-3.28, m, 1H, NCH; 3.60-3.88, m, 1H, NCH; 7.72, b, 2H, NH; 8.48, b, 3H, NH |
| A3 | | 1.00-2.20, m, 8H, $CCH_2$; 2.78, s, 3H, $NCH_3$; 3.05-3.32, m, 1H, NCH; 3.60-3.85, m, 1H, NCH; 8.50, b, 3H, NH |
| A4 | | 1.25-1.65, m, 4H, $CCH_2$; 1.70-2.20, m, 4H, $CCH_2$; 2.70-3.08, m, 4H, 3H from $NCH_3$ and 1H from NCH; 3.35-3.65, m, 1H, NCH; 8.35, b, 3H, NH |

EXAMPLE B

3-Amino-2-(trans-4-dimethylaminocyclohexyl)-1-methyl-guanidine a) 1-(trans-4-Dimethylaminocyclohexyl)-3-methyl-thiourea 0.90 g of Methyl-isothiocyanate are added to a solution of 1.74 g of trans-4-dimethylamino-cyclohexanamine in 50 ml of EtAc. The mixture obtained is stirred at RT, solvent is evaporated and 1-(4-dimethylaminocyclohexyl)-3-methyl-thiourea is obtained.

b) 1-(trans-4-Dimethylaminocyclohexyl)-2,3-dimethyl-isothiourea

A mixture of 0.50 g of 1-(4-dimethylaminocyclohexyl)-3-methyl-thiourea in 10 ml of MeOH, 1.16 ml of 2M HCl (in MeOH) and 0.36 g of methyliodide is stirred at RT. From the mixture obtained solvent is evaporated and the evaporation residue obtained is treated with $H_2O$. 10 ml of a strong basic ion exchanger in chloride form (Amberlite IRA 400 (Cl)$^R$) are added to the aqueous mixture obtained and the mixture obtained is stirred at RT. A precipitate obtained is filtrated off and the filtrate obtained is lyophilized. 1-(trans-4-Dimethylamino-cyclohexyl)-2,3-dimethyl-isothiourea in the form of a hydrochloride is obtained.

c) 3-Amino-2-(trans-4-dimethylaminocycloheyl)-1-methyl-guanidine

A solution of 0.71 g of 1-(4-dimethylaminocyclohexyl)-2,3-dimethyl-isothiourea in the form of a hydrochloride in 40 ml of EtOH absolute and 0.126 ml of hydrazine monohydrate is refluxed. From the mixture obtained solvent is evaporated and 3-amino-2-(trans-4-dimethylaminocyclohexylyl-methyl-guanidine in the form of a dihydrochloride is obtained. $^1$H-NMR: 1.12-1.55, m, 4H, $CCH_2$; 1.75-1.98, m, 4H, $CCH_2$; 2.30, b, 6H, $NCH_3$; 2.70, s, 3H, $NCH_3$; 3.20-3.80, m, 2H, NCH.

According to the method as set out in Example B, but using appropriate starting materials, the compounds of Example B2 and B3 of TABLE 5 below in the form of a hydrochloride are obtained. $^1$H-NMR-data of the compounds obtained are also set out in TABLE 5.

EXAMPLE C

[trans-4-((Hydrazino)methyliminomethyl)aminocyclohexyl]-trimethylammonium-chloride a) [trans-4-(2,3-Dimethyl-isothioureido)-cyclohexyl]-trimethylammoniumchloride A mixture of 0.50 g of 1-(4-dimethylamino-cyclohexyl)-3-methyl-thiourea in 20 ml of MeOH and 0.36 ml of methyliodide is stirred at RT. The mixture obtained is refluxed and solvent is evaporated. A residue formed is treated with $H_2O$, the aqueous mixture obtained is stirred in the presence of a strong basic ion exchanger in chloride form (Amberlite IRA 400 (Cl)$^R$), filtered and the filtrate obtained is subjected to lyophilisatlon. [trans-4-(2,3-Dimethyl-isothioureido)-cyclohexyl]-trimethylammoniumchloride is obtained.

b) [trans-4-((Hydrazino)methyliminomethyl)aminocyclohexyl]- trimethylammoniumchloride A solution of [trans-4-(2,3-dimethyl-isothioureido)-cyclohexyl]-trimethylammoiniumchloride in EtOH and 0.118 ml of hydrazine monohydrate is refluxed and from the mixture obtained solvent is evaporated. [trans-4-((Hydrazino)methyliminomethyl)aminocyclo hexyl]-trimethylammoniumchloride is obtained in the form of a hydrochloride. $^1$H-NMR: 1.40-1.70, m,4H,$CCH_2$;1.82-2.30, m, 4H, $CCH_2$; 2.80,s,3H, $NCH_3$; 3.05, b,9H,$NCH_3$; 3.30-3.50, m, 1H, NCH; 3.60-3.80, m, 1H, NCH.

According to the method as set out in Example C, but using appropriate starting materials, the compound of formula

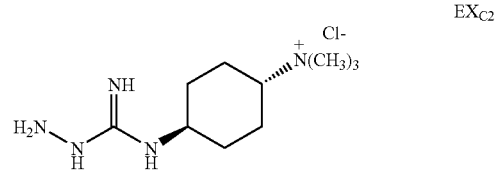

$EX_{C2}$

TABLE 5

| EX | Compound of formula | $^1$H-NMR |
|---|---|---|
| B2 | ![structure with N(CH3)2] | (D$_2$O) 1.22-1.70, m, 4H, $CCH_2$; 1.90-2.28, m, 4H, $CCH_2$; 2.70, b, 6H, $NCH_3$; 2.95-3.45, m, 2H, NCH |
| B3 | ![structure with NHCH3, NCH3, CH3] | 1.10-1.88, 6H, $CCH_2$; 1.90-2.18, m, 2H, $CCH_2$; 2.37, s, 3H, $NCH_3$; 2.76, s, 3H, $NCH_3$; 2.83, s, 3H, $NCH_3$; 3.32-3.62, m, 2H, NCH | in the form of a hydrochloride is obtained. ¹H-NMR: 1.18-1.70, m, 4H, CCH₂; 1.88-2.30, m, 4H, CCH₂; 3.05, b, 9H, NCH₃; 3.20-3.68, m, 2H, NCH.

EXAMPLE D

3-Amino-bis-1,2-trans-4-aminocyclohexyl)-3-methyl-guanidine a) Benzylidene derivative of 3-amino-bis-1,2-(trans-4-aminocyclohexyl)-3-methyl-guanidine S-methyl-2-methyl-isothiosemicarbazide is reacted with trans-1,4-diaminocyclohexane according to the method of Example 1a). Beside 3-amino-1-(trans-4-aminocyclohexyl)-3-methyl-guanidine in the form of a monohydrochloride, a side product is obtained which is purified by column chromatography (Li Chroprep RP-18ᴿ, Merck). The benzylidene derivative of 3-amino-bis-1,2-(trans-4-aminocyclohexyl)-3-methyl-guanidine in the form of a dihydrochloride is obtained.

b) 3-Amino-bis-1,2-(trans-4-aminocyclohexyl)-3-methyl-guanidine in the form of a trihydrochloride is obtained from the benzylidene derivative of 3-amino-bis-1,2-(trans-4-aminocyclohexyl)-3-methyl-guanidine in the form of a dihydrochloride according to the method of Example 1b). ¹H-NMR: (D₂O) 1.20-1.60, m, 8H, CCH₂; 1.80-2.18, m, 8H, CCH₂; 2.95-3.20, 5H, 3H from NCH₃ and 2H from NCH; 3.22-3.48, m, 2H, NCH.

Analogously as described in Example D, but using appropriate starting materials the compounds of Examples D1 to D10 as set out in TABLE 6 below in the form of a hydrochloride are obtained. ¹H-NMR data are also set out in TABLE 6.

TABLE 6

| EX | Compound of formula | ¹H-NMR |
|---|---|---|
| D1 | | 1.10-2.25, m, 8H, CCH₂; 2.88-3.12, m, 1H, NCH; 3.20, s, 3H, NCH₃; 3.52-3.85, m, 1H, NCH; 7.75, b, 2H, NH; 8.40, b, 3H, NH |
| D2 | | (D₂O) 1.25-1.60, m, 4H, CCH₂; 1.82-2.18, m, 4H, CCH₂; 3.00-3.20, 4H, 3H from NCH₃ and 1H from NCH; 3.22-3.45, m, 1H, NCH |
| D3 | | (D₂O) 1.50-1.90, m, 8H, CCH₂; 3.09, s, 3H, NCH₃; 3.20-3.40, m, 1H, NCH; 3.50-3.68, m, 1H, NCH |
| D4 | | |
| D5 | | (D₂O) 0.50-2.00, m, 10H, 8H from CCH₂ and 2H from CCH; 2.65-2.85, m, 2H, NCH₂, 2.92-3.30, m, 5H, 3H from NCH₃ and 2H from NCH₂ |
| D6 | | (D₂O) 0.50-2.00, m, 10H, 8H from CCH₂ and 2H from CCH; 2.80-2.95, m, 2H; NCH₂; 2.98-3.25, m, 5H, 3H from NCH₃ and 2H from NCH₂ |
| D7 | | (D₂O) 0.72-1.08, m, 4H, CCH2; 1.32-1.88, m, 6H, 4H from CCH₂ and 2H from CCH; 2.62-2.85, m, 2H, NCH₂; 2.90-3.25, m, 5H, 3H from NCH₃ and 2H from NCH₂ |

TABLE 6-continued

| EX | Compound of formula | $^1$H-NMR |
|---|---|---|
| D8 | H$_2$N-N(CH$_3$)-C(=NH)-NH-CH$_2$-C$_6$H$_4$-CH$_2$-NH$_2$ (para) | (D$_2$O) 3.17, s, 3H, NCH$_3$; 4.09, b, 2H, NCH$_2$; 4.42, b, 2H, NCH$_2$; 7.20-7.48, m, 4H, arom. H |
| D9 | H$_2$N-N(CH$_3$)-C(=NH)-NH-CH$_2$-C$_6$H$_4$-CH$_2$-NH$_2$ (meta) | (D$_2$O) 3.18, s, 3H, NCH$_3$; 4.09, b, 2H, NCH$_2$; 4.43, b, 2H, NCH$_2$; 7.20-7.55, m, 4H, arom. H |
| D10 | H$_2$N-N(CH$_3$)-C(=NH)-NH-CH$_2$-C$_6$H$_4$-NH$_2$ (meta) | |

EXAMPLE E

[trans-4-((1-Methylhydrazino)iminomethyl)aminocyclohexyl]-trimethyl-ammoniumchloride a) Benzylidene derivative of 3-amino-1-(trans-4-aminocyclohexyl)-3-methyl-quanidine The pH of a solution of 5 g of the benzylidene derivative of 3- amino-1-(trans-4-aminocyclo hexyl)-3-methyl-guanidine in the form of a monohydrochloride in H$_2$O is adjusted to pH 13.6 by addition of 8N NaOH. The mixture obtained is extracted with CH$_2$Cl$_2$. The organic phase obtained is dried and solvent is evaporated. The benzylidene derivative of 3-amino-1-(trans-4-aminocyclohexyl)-3-methyl-guanidine is obtained.

b) Benzylidene derivative of [trans-4-((1-methylhydrazino) iminomethyl))-aminocyclo-hexyl]-trimethylammoniumchloride 1.295 g of methyliodide in 10 ml of AcCN are added to a solution of 1 g of the benzylidene derivative of 3-amino-1-(trans-4-aminocyclohexyl)-3-methyl-guanidine in AcCN. The mixture obtained is refluxed and stirred at RT. Solvent is evaporated, the evaporation residue obtained is treated with H$_2$O and with 20 ml of a strong basic ion exchanger in chloride form. A suspension formed is stirred at RT, filtered and the filtrate obtained is subjected to lyophilisation. The lyophilizate obtained is treated with H$_2$O, the pH of the solution obtained is adjusted with 8N NaOH to pH 13.4, the mixture obtained is extracted with CH$_2$Cl$_2$, the aqueous phase obtained is adjusted with 8N HCl to pH 2 and the mixture obtained is lyophilised. The lyophilisate obtained is dissolved in H$_2$O and subjected to chromatography (Li-Chroprep RP-18$^R$, grain size 40-63 μm, Merck). Fractions containing the desired product are collected and lyophilized. The benzylidene derivative of [trans-4-((1-methylhydrazino)-(iminomethyl))aminocyclohexyl]-trimethylammoniumchloride in the form of a hydrochloride is obtained.

c) [trans-4-((1-Methylhydrazino)iminomethyl)-aminocyclohexyl]-trimethyl-ammoniumchloride hydrochloride A mixture of the benzylidene derivative of [trans-4-((1-methylhydrazino)(iminomethyl))-aminocyclohexyl]-trimethylammoniumchloride in 1.7 ml of 2N HCl and H$_2$O is treated by steam destillation. From the mixture obtained solvent is evaporated. [trans-4-((1-Methyl-hydrazino)iminomethyl) aminocyclohexyl]-trimethylammoniumchloride in the form of a hydrochloride is obtained. $^1$H-NMR: 1.35-1.72, m,4H,CCH$_2$; 1.82-2.30, m, 4H, CCH$_2$; 3.05, b, 9H, NCH$_3$; 3.20,s,$_1$H, NCH$_3$; 3.30-3.72, m, 2H, NCH; 7.45, d, J=4 Hz, 1H, NH; 7.74, b, 2H, NH.

EXAMPLE F

3-Amino-1-(trans-4-aminocyclohexyl)-3-ethyl-guanidine a) Benzylidene derivative of [trans-4-((hydrazino)iminomethyl)aminocyclohexyl]-1-N-formamide A mixture of 5.5 ml of acetic anhydride and 11.2 ml of formic acid is stirred at 0° and a solution of 5.04 g of benzylidene derivative of 3-amino-1-(trans4-aminocyclohexyl)-guanidine in 5.6 ml of formic acid are added. From the mixture obtained solvent is evaporated. The evaporaUon residue obtained is treated with H$_2$O and the pH of a solution formed is adjusted to 13.02 with 2N NaOH. A precipitate formed is filtered off, washed and dried. The benzylidene derivative of [trans-4-((hydrazino)iminomethyl)aminocyclo-hexyl]-1-N-formamide is obtained.

b) Benzylidene derivative of [trans-4-((1-ethylhydrazino) iminomethyl)aminocyclo-hexyl]-1-N-formamide A mixture of 0.28 ml of ethyliodide and of a solution of 0.5 g of the benzylidene derivative of [trans-4-((1-hydrazino) (iminomethyl)aminocyclohexyl]-N-formamide is refluxed. The mixture obtained is kept overnight at RT and further ethyliodide is added. The mixture obtained is refluxed and the mixture obtained again is kept at RT. A precipitate forms, which is filtered off and dried. The benzylidene derivative of

[trans-4-((1-ethylhydrazino)iminomethyl)amino cyclohexyl]-1-N-formamid in the form of a hydroiodide is obtained.

c) 3-Amino-1-(trans-4-aminocyclohexyl)-3-ethyl-quanidine

A suspension of 0.34 g of the benzylidene derivative of [trans-4-((1-ethylhydrazino)-iminomethyl)aminocyclohexyl]-1-N-formamide in the form of a hydroiodide in 10 ml of $H_2O$ and 10 ml of strong basic ion exchanger in chloride form is stirred. The mixture obtained is filtrated and the filtrate obtained is treated with 2 ml of 2N HCl, benzaldehyde and formic acid are distilled off and solvent is evaporated. 3-Amino-1-(trans-4-aminocyclohexyl)-3-ethyl-guanidine in the form of a dihydrochloride is obtained. $^1$H-NMR: ($D_2O$) 0.88-1.75, m, 6H, 4H from $CCH_2$ and 3H from $CCH_3$; 1.80-2.35, m, 4H, $CCH_2$; 2.90-3.70, m, 4H, 2H from $NCH_2$ and 2H from NCH.

According to the method as described in Example F, but using appropriate starting materials the compound of formula

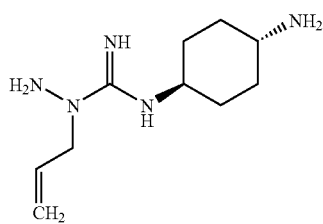

EX$_{F2}$ in the form of a hydrochloride is obtained. $^1$H-NMR: ($D_2O$) 1.20-1.65, m, 4H, $CCH_2$; 1.80-2.22, m, 4H, $CCH_2$; 3.00-3.20, m, 1H, NCH; 3.22-3.52, m, 1H, NCH; 3.88-4.20, m, 2H, $NCH_2$; 4.98-5.40, m, 2H, C=$CH_2$; 5.55-5.88, m, 1H, CH=C.

EXAMPLE G

4-Amino-N-[trans-4-((1-methylhydrazino)iminomethyl)aminocyclohexyl]-benzene-sulfonamide a) Benzylidene Derivative of N-[4-[-trans-4-((1-methylhydrazino)iminomethyl)]-aminocyclohexylsulfamoyl)-phenyl]acetamide 2.37 ml of N,O-bis-(trimethylsilyl)-acetamide are added to a suspension of 0.5 g of the benzylidene derivative of 3-amino-1-(trans-4-aminocyclohexyl)-3methyl-guanidine in AcCN. A solution obtained is treated with 0.378 g of 4-acetylamino-benzenesulfonyl chloride and stirred at RT. To the mixture obtained 3.49 ml of $H_2O$/AcCN are added, a precipitate formed is filtrated off, washed and dried. The benzylidene derivative of N-[4-[-trans-4-((1-methyl-hydrazino)iminomethyl)]aminocyclohexylsulfamoyl)-phenyl]acetamide is obtained.

b) 4-Amino-N-[trans-4-((1-methylhydrazino)iminomethyl)aminocyclohexyl]benzene- sulfonamide A mixture of 0.62 g of the benzylidene derivative of N-[4-[trans-4-((1-methylhydrazino)imino-methyl)]aminocyclohexylsulfamoyl)phenyl]acetamide is treated with 3.4 ml of 1 N HCl and $H_2O$. The aqueous solution obtained is concentrated and dried. 4-Amino-N-[trans-4-((1-methylhydrazino)iminomethyl)aminocyclohexyl]-benzene-sulfonamide in the form of a dihydrochloride is obtained. $^1$H-NMR: 1.10-1.40, m, 4H, $CCH_2$; 1.50-1.80, m, 4H, $CCH_2$; 2.65-2.90, m, 1H, NCH; 3.10, s, 3H, $NCH_3$; 3.20-3.50, m, 1H, NCH; 6.85, d, J=4 Hz, 2H, aromatic-H; 7.52, d, J=4 Hz, 2H, aromatic-H.

EXAMPLE H

3-Amino-1-(trans-4-aminocyclohexyl)-2,3-dimethyl-quanidine a) [trans-4-(3-Amino-3-methyl-thioureido)cyclohexyl] carbamic acid tert-butylester 0.49 ml of methylhydrazine are added to a solution of 2 g of (trans-4-isothiocyanate-cyclohexyl)carbamic acid tert-butylester. The mixture obtained Is stirred at RT and petrolether is added. A precipitate formed is filtrated off, washed and dried. [trans4-(3-Amino-3-methyl-thioureido) cyclohexyl]carbamic acid tert-butylester is obtained.

b) [trans-4-(3-Amino-2,3-dimethyl-isothioureido)cyclohexyl]-carbamic acid tert-butylester A suspension of 1.17 g of [trans-4-(3-amino-3-methyl-thioureldo)cyclohexyl]carbamic acid tert-butylester in 30 ml of MeOH is treated with 0.34 ml of methyliodide, the mixture obtained is refluxed and solvent is evaporated. The evaporation residue obtained Is suspended in $H_2O$ and treated with a strong basic ion exchanger in chloride form. The mixture obtained is stirred at RT, the ion exchanger is filtered off and the filtrate obtained is lyophilised. [trans4-(3-Amino-2,3-dimethyl-isothioureido) cyclohexyl]carbamic acid tert-butylester in the form of a hydrochloride is obtained.

c) Benzylidene Derivative of [trans-4-(3-amino-2,3dimethyl-isothioureido)cyclohexyl]-carbamic acid tert-butyl ester 1.3 ml of 2N HCl and 0.15 ml of benzaldehyde are added to a solution of 0.40 g of [trans4-(3-amino-2,3-dimethyl-isothioureido)cyclohexyl]carbamic acid tert-butylester in the form of a hydrochloride in 20 ml of $H_2O$ and 30 ml of AcCN. The mixture obtained is stirred, AcCN is evaporated and a solution obtained is extracted with ether. The pH of the aqueous phase obtained is adjusted to pH 7 and a precipitate formed Is filtrated off, washed and dried. The benzylidene derivative of [trans-4-(3-amino-2,3-dimethyl-isothioureido) cyclohexyl]carbamic acid tert-butylester in the form of a hydrochloride is obtained.

d) Benzylidene Derivative of [trans-4-(1-methylhydrazino) (methyliminomethyl)amino-cyclohexyl]carbamic acid tert-butylester A suspension of 0.2 g of the benzylidene derivative of [trans-4-(3-amino-2,3-dimethyl-isothioureido)cyclohexyl] carbamic acid tert-butylester in the form of a hydrochloride is treated with 0.126 ml of methylamine (33% in EtOH abs.) and stirred. From the mixture obtained solvent is evaporated and the benzylidene derivative of [trans-4-(1-methylhydrazino) (methyl iminomethyl)aminocyclohexyl]carbamic acid tert-butylester is obtained.

e) Benzylidene derivative of 3-amino-1-(trans-4-aminocyclohexyl)-2,3-dimethyl-guanidine 10 ml of TFA are added to a solution of 0.2 g of the benzylidene derivative of [trans-4-(1-methylhydrazino)(methyl-iminomethyl)aminocyclohexyl]carbamic acid tert-butylester in 10 ml of $CH_2Cl_2$ at 0°. The mixture obtained is stirred at RT, solvent is evaporated and the benzylidene derivative of 3-amino-1-(trans-4-aminocyclohexyl)-2,3-dimethyl-guanidine in the form of a trifluoroacetate is obtained.

f) 3-Amino-1-(trans-4-aminocyclohexyl)-2,3-dimethyl-guanidine 1.6 ml of 1N HCl are added to a solution of 0.2 g of the benzylidene derivative of 3-amino-1-(trans-4-amino-cyclohexyl)-2,3-dimethyl-guanidine in the form of a trifluoroacetate in H$_2$O (benzaldehyde is split off). The volume of the mixture obtained is concentrated and 20 ml of strong basic ion exchanger in chloride form are added. The mixture obtained Is stirred, filtrated and solvent from the filtrate obtained is evaporated. 3-Amino-1-(trans-4-aminocyclo hexyl)-2,3-dimethyl-guanidine in the form of a dihydrochloride is obtained. $^1$H-NMR: 1.30-1.65, m, 4H, CCH$_2$; 1.78-2.15, m, 4H, CCH$_2$; 2.70-3.00, m, 4H, 3H from NCH$_3$ and 1H from NCH; 3.14, s, 3H, NCH$_3$; 3.22-3.55, m, 1H, NCH; 8.19, b, 3H, NH.

According to the method as described in Example H, but using appropriate starting materials, the compounds of formulae EX$_{H2}$, EX$_{H3}$ and EX$_{H4}$ in the form of a hydrochloride are obtained:

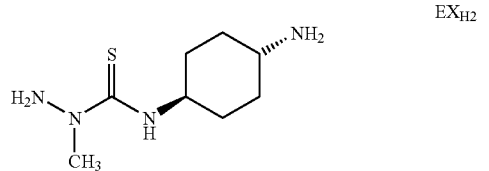

EX$_{H2}$ $^1$H-NMR: (DMSO-d$_8$/D$_2$O) 1.20-1.50, m, 4H, CCH$_2$; 1.78-2.02, m, 4H, CCH$_2$; 2.80-3.10, m, 1H, NCH; 3.40, s, 3H, NCH$_3$; 3.80-4.05, m, 1H, NCH.

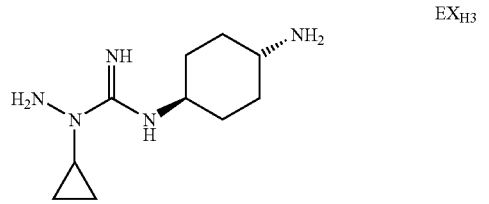

EX$_{H3}$ (the BOC-protecting group is removed with HCl in MeOH).

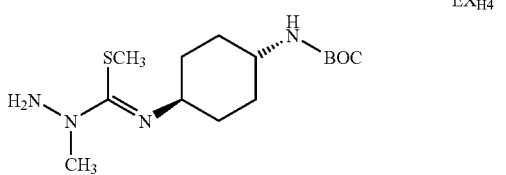

EX$_{H4}$ $^1$H-NMR: 1.00-1.92, m, 17H, 9H from CCH$_3$ and 8H from CCH$_2$; 2.56, s, 3H, SCH$_3$; 3.00-3.25, m, 1H, NCH; 3.51, s, 3H, NCH$_3$; 3.68-3.92, m, 1H, NCH (the BOC protecting group is removed with TFA).

EXAMPLE I

[3-Amino-1-(trans-4-aminocyclohexyl)-3-methyl]-urea a [trans-4-(3-Amino-3-methyl-ureido)cyclohexyl-carbamic acid tert-butylester A solution of 0.435 g (trans-4-(3-amino-2,3-dimethyl-isothioureido)cyclohexyl]-carbamic acid tert-butyl ester hydrochloride is treated with 0.18 ml of NH$_3$ (2M in EtOH) and the mixture obtained is refluxed and stirred at RT. From the mixture obtained solvent is evaporated and [trans-4-(3-amino-3-methyl-ureido)cyclohexyl-carbamic acid tert-butylester is obtained.

$^1$HNMR: 1.00-1.50, m, 13H, 9H from CCH$_3$ and 4H from CCH$_2$; 1.60-1.90, m 4H, CCH$_2$; 3.08, s, 3H, NCH$_3$; 3.25-3.80, m, 2H, NCH b) [3-Amino-1-(trans-4-aminocyclohexyl)-3methyl]-urea A mixture of 0.34 g of [trans-4-(3-amino-3-methyl-ureido) cyclohexyl-carbamic acid tert-butyl ester in 15 ml of MeOH and 2 ml of 2N HCl (in MeOH) is stirred at RT for 4 hours. From the mixture obtained solvent is evaporated, the evaporation residue is treated with H$_2$O and the pH of the mixture obtained is adjusted with 2N HCl to pH 2. A precipitate formed is filtered off. The filtrate obtained is lyophilized. [3-Amino-1-(trans-4-aminocyclo-hexyl)-3-methyl]-urea in the form of a dihydrochloride is obtained.

EXAMPLE J

3-Amino-1-(trans-4-aminocyclohexyl)-1,2-dimethyl-guananidine a) (4-Methylamino-cyclohexyl)carbamic acid benzylester A mixture of 3.31 ml of methylamine (33% in absolute EtOH), 4.63 ml of acetic acid and 75 ml of MeOH are added dropwise to a solution of 10 g of (4-oxo-cyclohexyl)carbamic acid benzylester in 27 ml of MeOH. To the mixture obtained a solution of 5 g of sodiumcyano-borhydride in 25 ml of MeOH are added and the mixture obtained is stirred for 72 hours at RT. From the mixture obtained solvent is evaporated, 45 ml of 1N NaOH are added and the mixture obtained is kept at 60° for 40 minutes. The mixture obtained is extracted with CH$_2$Cl$_2$, the organic layer obtained is dried and solvent is evaporated. The evaporation residue obtained is treated with 142 ml of 2-methoxy-2-methyl-propane and the suspension obtained is refluxed for 30 minutes. The mixture obtained Is filtered. (4-Methylamino-cyclohexyl)carbamic acid benzylester wherein (4-trans-methylamino-cyclohexyl)carbamic acid benzylester is enriched (precipitate) and (4-Methylamino-cyclohexyl)carbamic acid benzylester wherein (4-cis-methylamino-cyclohexyl)carbamic acid benzylester is enriched (filtrate) is obtained. From the sample comprising enriched (4-cis-methylamino-cyclohexyl)carbamic acid benzylester, solvent is evaporated.

Each enriched sample obtained is treated with 50 ml of 2M HCl, the suspension obtained is filtered, the pH of the filtrate obtained is adjusted to pH 11.8, and the mixture obtained is extracted with CH$_2$Cl$_2$. From the organic phase obtained solvent is evaporated.

2 Products, i.e. (4-methylamino-cyclohexyl)-carbamic add benzylester a. wherein (trans-4-methylamino-cyclohexyl)-carbamic acid benzylester is enriched b. wherein (cis-4-methylamino-cyclohexyl)carbamic acid benzylester is enriched, are obtained.

b) [4-(1,3-Dimethyl-thioureido)-cyclohexyl]carbamic acid benzylester

A solution of 0.14 g of methylisothiocyanate in 7 ml of CH$_2$Cl$_2$ is adde dropwise to a solution of 0.5 g of the enriched (trans4-methylamino-cyclohexyl)-carbamic acid benzylester in 10 ml of CH$_2$Cl$_2$, the mixture obtained is stirred for 16 hours at RT and from the mixture obtained solvent is evaporated. [4-(1,3-Dimethyl-thioureido)-cyclohexyl]carbamic acid benzylester is obtained.

c) [4-(1,2,3-Trimethyl-isothioureido)-cyclohexyl]carbamic acid benzylester 0.18 ml of methyliodide are added to a solution of 0.64 g [4-(1,3-dimethyl-thioureido)-cyclohexyl]carbamic acid benzylester in 30 ml of AcCN. The mixture obtained is refluxed for 2.5 hours and solvent is evaporated. [4-(1,2,3-Trimethyl-isothioureido)-cyclohexyl]-carbamic acid benzylester in the form of a hydroiodide is obtained.

d) [4-(3-Amino-1,2-dimethyl-guanidino)cyclohexyl]carbamic acid benzylester 0.84 g of [4-(1,2,3-trimethyl-isothioureido)-cyclohexyl] carbamic acid benzylester in the form of a hydroiodide are stirred with 10 ml of of a strong basic ion exchanger in chloride form. A suspension obtained is filtered and the filtrate obtained is lyophilized. The lyophilisate is treated with 15 ml of EtOH and with 0.08 ml of hydrazine monohydrate. The mixture obtained is refluxed for 2.5 hours and from the mixture obtained solvent is evaporated. [4-(3-Amino-1,2-dimethyl-guanidino)-cyclohexyl]-carbamic acid benzylester in the form of a hydrochloride is obtained.

e) 3-Amino-1-(4-aminocyclohexyl)-1,2-dimethyl-guanidine

A solution of 0.50 g of [4-(3-amino-1,2-dimethyl-guanidino)-cyclohexyl]carbamic acid benzylester in the form of a hydrochloride in 25 ml of $CH_2Cl_2$ is treated with 0.77 ml of bortribromide. The mixture obtained is stirred for for 30 minutes at RT, the precipitate formed is filtered off and washed with $CH_2Cl_2$. The precipitate obtained is dissolved in $H_2O$, treated with 10 ml of strong basic ion exchanger in chloride form and stirred for 2 hours at RT. From the mixture obtained the ion exchanger is filtered off and solvent is evaporated from the filtrate obtained. 3-Amino-1-(4-aminocyclohexyl)-1,2-dimethyl-guanidine in the form of a dihydrochloride is obtained. The ratio trans/cis is about 0.7:0.3 ($^1$H-NMR data-estimation).

EXAMPLE K

3-Amino-1-(cis-4-aminocyclohexyl)-1,2,3-trimethyl-guanidine a) Benzylidene Derivative of 3-amino-1-(cis-4-aminocyclohexyl)-1,2-dimethyl-guanidine A solution of 1.73 g of 3-amino-1-(cis-4-aminocyclohexyl)-1,2-dimethyl-guanidine in the form of a dihydrochloride in 40 ml of $H_2O$ is acidified with 2M HCl and treated with 0.88 ml of benzaldehyde. The mixture obtained is stirred for 3 hours at RT and the excess of benzaldehyde is extracted with diethylether. An aqueous solution of the crude benzylidene derivative of 3-amino-1-(cis-4-aminocyclohexyl)-1,2-dimethyl-guanidine in the form of a hydrochloride is obtained and subjected to chromatography (LiChroprep RP-18$^R$, Merck, grain size 40-63 μm). Fractions containing the desired product are combined. The benzylidene derivative of 3-amino-1-(cis-4-aminocyclohexyl)-1,2-dimethyl-guanidine in the form of a monohydrochloride is obtained. The pH of an aqueous solution of benzylidene derivative of 3-amino-1-(cis-4-aminocyclohexyl1,2-dimethyl-guanidine monohydrochloride is adjusted with 2M NaOH to pH 13, the mixture obtained is extracted with $CH_2Cl_2$, the organic phase obtained is dried and solvent is evaporated. The benzylidene derivative of 3-amino-1-(cis-4-aminocyclohexyl)-1,2-dimethyl-guanidine is obtained.

b) Benzylidene Derivative of [cis-4-((hydrazino)methyliminomethyl)-methylaminocyclohexyl]-1-N-formamide A mixture of 1.08 ml of formic acid and 0.53 ml of acetic anhydride is stirred for 30 minutes at 0° (mixed anhydride formation), and a solution of 0.54 g of benzylidene derivative of 3-amino-1-(cis-4-aminocyclohexyl)-1,2-dimethyl-guanidine in 1.08 ml of formic acid are added dropwise. The mixture obtained is stirred overnight at RT. Solvent is evaporated and the evaporation residue obtained is treated with 40 ml of $H_2O$. The pH of the solution obtained is adjusted with 2M NaOH to pH 13 and the mixtrue obtained is extracted with $CH_2Cl_2$. The organic layer obtained is dried and solvent is evaporated. The benzylidene derivative of [cis-4-((hydrazino)methyliminomethyl)-methylaminocyclohexyl]-1-N-formamid is obtained.

c) Benzylidene Derivative of 3-amino-1-(cis-4-aminocyclohexyl)-1,2,3-trimethyl-guanidine A mixture of 0.59 g of the benzylidene derivative of [(cis-4-((hydrazino)methyl-iminomethyl)-methylaminocydohexyl]-1-N-formamide in 40 ml of AcCN and 0.29 ml of methyliodide is refluxed for 4 hours and solvent is evaporated from the mixture obtained. The evaporation residue obtained is treated with 40 ml of $H_2O$ and 10 ml of strong basic Ion exchanger In chloride form. The suspension obtained is stirred for 1 hour at RT, the ion exchanger is filtered off and to the filtrate obtained 5 ml of 2M HCl are added. The solution obtained is subjected to steam distillation for 4 hours (complete removal of the formyl group and partial removal of the benzylidene protecting group). In order to fully protect again the hydrazino group, the solution obtained is stirred with 0.38 ml of benzaldehyde for 2 hours at RT and extracted three times with diethylether. The aqueous solution obtained is subjected to chromatography (LiChroprep RP$^{18}$). Fractions containing the desired product are combined, solvent is evaporated and the benzylidene derivative of 3-amino-1-(cis-4-aminocyclohexyl)-1,2,3-trimethyl-guanidine in the form of a hydrochloride is obtained.

d) 3-Amio-1-(cis-4-aminocyclohexyl)-1,2,3-trimethyl-guanidine

Benzaldehyde is distilled off from a mixture of the benzylidene derivative of 0.32 g of 3-amino-1-(cis-4-aminocydohexyl)-1,2,3-trimethyl-guanidine in the form of a hydrochloride in 5 ml of HCl and $H_2O$. From the mixture obtained solvent is evaporated and 3-amino-1-(cis-4-aminocyclohexyl)-1,2,3-trimethyl-guanidine in the form of a dihydrochlorid is obtained.

EXAMPLE L

3-Amino-1-(trans-4-ethylaminocyclohexyl)-3-methyl-guanidine and 3-Amino-1-(trans-4-diethylaminocyclohexyl)-3-methyl-guanidine a) Benzylidene derivative of 3-amino-1-(trans-4-ethylaminocyclohexyl)-3-methyl-guanidine and benzylidene derivative of 3-amino-1-(trans-4-diethyl-aminocyclohexyl)-3-methyl- guanidine A solution of 0.73 g of the benzylidene derivative of 3-amino-1-(trans-4-aminocyclohexyl)-3-methyl-guanidine and 0.47 ml of N-ethyidiisopropylamine in 40 ml of AcCN is treated with 0.28 ml of ethyliodide. The mixture obtained is refluxed for 6 hours and solvent is evaporated. A mixture of 3-amino-1-(trans4-ethylaminocyclohexyl)-3-methyl-guanidine in the form of a dihydrochloride and 3-amino-1-(trans-4-diethylaminocyclohexyl)-3 -methyl-guanidine in the form of a dihydrochloride is obtained.

b) Benzylidene derivative of 3-amino-1-(trans-4-ethylaminocyclohexyl)-3-methyl-guanidine and benzylidene Derivative of 3-amino-1-(trans-4-diethyl-aminocyclohexyl)-3-methyl- guanidine A solution of 1.29 g of a mixture of 3-amino-1-(trans-4-ethylaminocyclohexyl)-3-methyl-guanidine in the form of a dihydrochloride and 3-amino-1-(trans-4-diethylaminocyclohexyl)-3-methyl-guanidine in the form of a dihydrochloride Is treated with 15 ml of a strong basic ion changer in chloride form, the suspension obtained is stirred for 1 hour at RT, the ion exchanger is filtered off, the filtrate obtained is acidified with 2M HCl and subjected to chromatography (LiChroprep RP[18]). Two products are eluted and the benzylidene derivative of 3-amino-1-(trans-4-ethylaminocyclohexyl)-3-methyl-guanidine in the form of a hydrochloride and the benzylidene derivative of 3-amino-1-(trans-4-diethylaminocyclohexyl)-3-methyl-guanidine in the form of a hydrochloride are obtained in pure form.

c) 3-Amino-1-(trans-diethylaminocyclohexyl)-3-methyl-guanidine

Removal of the benzylidene protecting group from the benzylidene derivative of 3-amino-1-(trans-4-diethylaminocyclohexyl)-3-methyl-guanidine in the form of a hydrochloride is performed according to the method of Example K d).

According to the method described in Examle L, but using appropriate starting materials, the compounds L1 to L6 of TABLE 7 below in the form of a hydrochloride are obtained:

TABLE 7

| EX | Compound of formula |
|---|---|
| L1 | 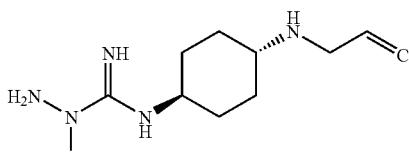 |
| L2 | 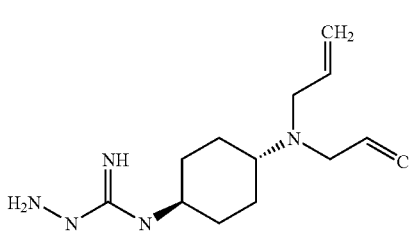 |
| L3 | 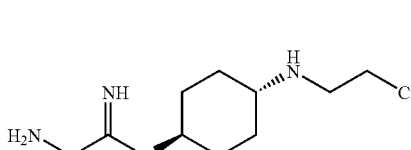 |

TABLE 7-continued

| EX | Compound of formula |
|---|---|
| L4 | 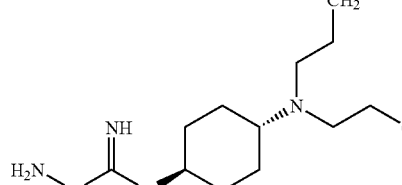 |
| L5 | 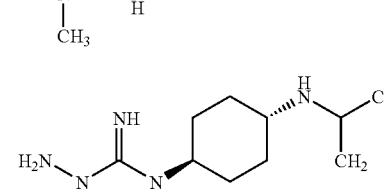 |
| L6 | 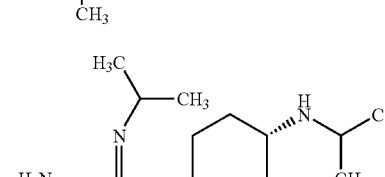 |

EXAMPLE M

3-Amino-1-(trans-4-aminocyclohexyl)-1-methyl-guanidine a) [(trans-4-Benzylidene-amino)-cyclohexyl]-methyl-cyanamide 2 ml of benzaldehyde are added to 2.53 g of trans-N-methyl-cyclohexan-1,4-diamine in 80 ml of toluene in one single portion. The mixture obtained is refluxed for 4 hours, cooled to RT, 6.9 ml of N-ethyl-diisopropylamin are added and a solution of 2.09 g of cyanogen bromide in 10 ml of toluene are added dropwise. The mixture obtained is stirred overnight at RT. A precipitate formed is filtered off, solvent from the filtrate obtained is evaporated, the evaporation residue obtained is treated with $H_2O$ and extracted with diethyl-ether. The organic layer obtained is dried and solvent is evaporated. [(trans-4-Benzylidene-amino)-cyclohexyl]-methyl-cyanamide is obtained.

b) 1-(trans-4-Aminocyclohexyl)-1-methyl-thiourea 20 ml of EtOH saturated with 3 g of $H_2S$ are added to a solution of 4.23 g of [(trans-4-benzylidene-amino)-cyclohexyl]-methyl-cyanamide and 4.1 ml of triethylamine in 60 ml of EtOH. The mixture obtained is heated in an autoclave for 4 hours at 120°. From the mixture obtained solvent and excess of $H_2S$ are removed by distillation. The distillation residue obtained is treated with 20 ml of 2M HCl and 10 ml of $H_2O$ and 50 ml of a strong basic ion changer in chloride form are added. The suspension obtained is stirred for 1 hour, the ion exchanger is filtrated off and the acidic filtrate obtained is subjected to chromatography (UChroprep RP-18[R], Merck, grain size 40-63 μm). 1-(trans-4 -Aminocyclohexyl)-1-methyl-thiourea in the form of a hydrochloride is obtained.

c) 1-(trans-4-Aminocyclohexyl)-1,2-dimethyl-isothiourea

A mixture of 0.6 g of 1-(trans-4-aminocyclohexyl)-1-methyl-thiourea in the form of a hydrochloride in 30 ml of MeOH and 0.22 ml of methyliodide is refluxed for 2 hours, solvent is evaporated and 1-(trans-4-aminocyclohexyl)-1,2-dimethyl-isothiourea in the form of a hydrochloride and a hydroiodide is obtained.

d) 3-Amino-1-(trans-4-aminocyclohexyl)-1-methyl-guanidine

A solution of 0.50 g of 1-(trans-4-aminocyclohexyl)- 1,2-dimethyl-isothiourea in the form of hydrochloride and a hydroiodide in 40 ml of EtOH is treated with 0.15 ml of hydrazine monohydrate and the mixture obtained is refluxed for 2 hours. Solvent from the mixture obtained is evaporated, the evaporation residue obtained is treated with 20 ml of $H_2O$ and to the mixture obtained 10 ml of a strong basic ion changer in chloride form are added. The suspension obtained is stirred for 1 hour, the ion exchanger is filtered off, from the filtrate obtained solvent is evaporated and 3-amino-1-(trans-4- aminocyclohexyl)-1-methyl-guanidine in the form of a dihydrochloride is obtained.

EXAMPLE N

3-Amino-1-(trans-4-aminocyclohexyl)-1,3-dimethyl-guanidine a) Benzylidene Derivative of 3-amino-1-(trans-4-aminocyclohexyl)-1-methyl-guanidine A solution of 0.79 g of 3-amino-1-(trans-4-aminocyclohexyl)-1-methyl-guanidine in the form of a dihydrochloride in 20 ml of $H_2O$ is treated with 0.46 ml of benzaldehyde and the mixture obtained is stirred overnight. The mixture obtained is extracted with diethylether and the aqueous layer obtained is subjected to chromatography. The product Is eluted and desired fractions are combined, the pH of the solution obtained is adjusted with 2M NaOH to pH 13 and the mixture obtained is extracted with $CH_2Cl_2$. The organic layer obtained is dried and solvent is evaporated. The benzylidene derivative of 3-amino-1-(trans-4-aminocyclohexyl)-1-methyl-guanidine is obtained.

b) Benzylidene Derivative of [trans-4-((hydrazino) iminomethyl)methylaminocyclo-hexyl]-acetamide 0.06 ml of acetylchloride are added to a suspension of 0.22 g of the benzylidene derivative of 3-amino-1-(trans-4-aminocyclohexyl)-1-methyl-guanidine and 0.08 g of $K_2CO_3$ in 15 ml of $CH_2Cl_2$, the mixture obtained is stirred for 4 hours at RT and solvent is evaporated. The evaporation residue obtained is treated with 20 ml of $H_2O$ and the pH of the solution obtained is adjusted with 2M NaOH to pH 13. The mixture obtained is extracted with $CH_2Cl_2$, dried and solvent is evaporated. The benzylidene derivative of [trans-4-((hydrazino)-iminomethyl)methylaminocyclohexyl]-acetamide is obtained.

c) Benzylidene Derivative of [trans-4-((1-methylhydrazino) iminomethyl) methylamino-cyclohexyl]-acetamide A mixture of 0.23 g of the benzylidene derivative of [trans-4-((hydrazino) iminomethyl) methylamino-cyclohexyl]-acetamide, 20 ml of AcCN and 0.1 ml of methyliodide Is refluxed for 4 hours. From the mixture obtained solvent is evaporated and the benzylidene derivative of [trans-4-((1-methylhydrazino) iminomethyl) methylaminocyclohexyl]-acetamide is obtained in the form of a hydrolodide.

d) 3-Amino-1-(trans-4-aminocyclohexyl)-1,3-dimethyl-guanidine

To 0.30 g of the benzylidene derivative of [trans4-((1-methylhydrazino) iminomethyl)methyl-aminocyclohexyl]-acetamide in the form of a hydroiodide in 20 ml of $_2O$, a strong basic Ion exchanger in chloride form is added and the suspension obtained is stirred for 1 hour. The ion exchanger is filtrated off and, 5 ml of 2M HCl are added to the filtrate obtained.

The mixture obtained is subjected to steam distillation (both protecting groups, i.e. the benzylidene and the acetyl group are removed), from the mixture obtained solvent is evaporated and 3-amino-1-(trans-4-aminocyclohexyl)-1,3-dimethyl-guanidine in the form of a dihydrochloride is obtained.

$^1$H-NMR-Spectra (200 MHz, in DMSO-$d_6$ Unless Given Otherwise)

1. 40-2.12, m, 8H, $CCH_2$; 3.10-3.30, m, 1H, NCH; 3.35, s, 3H, $NCH_3$; 3.55 and 4.54, AB-quartet, J=18 Hz, 2H, $SCH_2$; 3.75-3.95, m, 1H, NCH; 5.15, d, J=5 Hz, 1H, β-lactam; 5.77, d, J=55 Hz, 2H, $CH_2F$; 5.78, dd, J=5 Hz and 8 Hz, 1H, β-lactam; 8.12, s, 1H, CH=N; 9.86, d, J=8 Hz, 1H, NH 3 1.06, t, J=5 Hz, 3H, $CH_3$; 1.32-1.70, m, 4H, $CCH_2$; 1.75-2.12, m, 4H, $CCH_2$; 2.88-3.10, m, 1H, NCH; 3.48-3.72, m, 2H, 1H from $SCH_2$ and 1H from NCH; 3.98, m, 2H, $NCH_2$; 4.24, part of the AB-quartet, J=18 Hz, 1H, $SCH_2$; 5.14, d, J=5 Hz, 1H, β-lactam; 5.79, d, J=55 Hz, 2H, $CH_2F$; 5.77, dd, J=5 Hz and 8 Hz, 1H, β-lactam; 8.12, s, 1H, CH=N; 9.84, d, J=8 Hz, 1H, NH 4 (in $D_2O$) 1.28-1.65, m, 4H, $CCH_2$; 1.80-2.10, m, 4H, $CCH_2$; 2.82-3.08, m, 1H, NCH; 3.32-3.60, m, 2H, 1H from $NCH_2$ and 1 H from $SCH_2$; 4.14, part of the AB-quartet, J=18 Hz, 1H, $SCH_2$; 5.09, d, J=5 Hz, 1H, β-lactam; 5.69, d, 1H, β-lactam; 6.65, s, 1H, CH thiazol; 8.21, s, 1H, CH=N 5 1.35-1.68, m, 4H, $CCH_2$; 1.78-2.12, m, 4H, $CCH_2$; 2.82-3.06, m, 1H, NCH; 3.35, s, 3H, $NCH_3$; 3.50-3.80, m, 2H, 1H from NCH and 1H from $SCH_2$; 3.90, s, 3H, $OCH_3$; 4.58, part of the AB-quartet, J=18 Hz, 1H, $SCH_2$; 5.28, d, J=5 Hz, 1H, β-lactam; 5.90, dd, J=5 Hz and 8 Hz, 1H, β-lactam; 6.85, s,1 H, CH thiazol; 8.08, s, 1H, CH=N; 9.79, d, J=8 Hz,1H, NH 6 1.30-1.70, m, 4H, $CCH_2$; 1.82-2.08, m, 4H, $CCH_2$; 2.88-3.10, m, 1H, NCH; 3.40-3.68, m, 2H, 1H from NCH and 1H from $SCH_2$; 4.42-4.78, m, 3H, 2H from $NCH_2$ and 1H from $SCH_2$; 4.92-5.35, m, 3H, 1H from β-lactam and 2H from $CH_2$=C; 5.52-6.04, m, 4H, 1H from β-lactam, 1H from C—CH=C and 2H from $CH_2F$; 8.08, s, 1H, CH=N; 9.84, d, J=8 Hz, 1H, NH 7 1.15-1.50, m, 4H, $CCH_2$; 1.60-1.82, m, 2H, $CCH_2$; 1.88-2.20, m, 2H, $CCH_2$; 3.00-3.30, m, 1H, NCH; 3.45-3.75, m, 2H, 1H from NCH and 1H from $SCH_2$; 4.52, part of the AB-quartet, J=18 Hz, 1H, $SCH_2$; 5.28, d, J=5 Hz, 1H, β-lactam; 5.78, d, J=55 Hz, 2H, $CH_2F$; 5.92, dd, J=5 Hz and 8 Hz, 1H, β-lactam; 8.32, s, 1H, CH=N; 9.82, d, J=8 Hz, 1H, NH 8 1.28-1.62, m, 4H, $NCH_2$; 1.78-2.12, m, 4H, $NCH_2$; 2.88-3.12, m, 1H, NCH; 3.40-3.70, m, 2H, 1H from NCH and 1H from $SCH_2$; 4.48, part of the AB-quartet, J=18 Hz, 1H, $SCH_2$; 5.27, d, J=5 Hz, 1H, β-lactam; 5.77, d, J=55 Hz, 2H, $CH_2F$; 5.90, dd, J=5 Hz and 8 Hz, 1H, β-lactam; 8.28, s, 1H, CH=N; 10.82, d, J=8 Hz, 1H, NH 9 1.20-1.65, m, 4H, $CCH_2$; 1.90-2.12, m, 4H, $CCH_2$; 2.75, b, 6H, $NCH_3$; 3.00-3.60, m, 3H, 2 from NCH and 1H from $SCH_2$; 4.32, part of the AB-quartet, J=18 Hz, 1H, $SCH_2$;

5.22, d, J=5 Hz, 1H, β-lactam; 5.79, d, J=55 Hz, 2H, CH$_2$F; 5.80, dd, J=5 Hz and 8 Hz, 1H, β-lactam; 8.22, s, 1H, CH=N; 9.78, d, J=8 Hz, 1H, NH 10 1.30-1.70, m, 4H, CCH$_2$; 1.92-2.32, m, 4H, CCH$_2$; 3.05, b, 9H, NCH$_3$; 3.20-3.68, m, 3H, 2H from NCH and 1H from SCH$_2$; 4.48, part of the AB-quartet, J=18 Hz, 1H, SCH$_2$; 5.28, d, J=5 Hz, 1H, β-lactam; 5.78, d, J=55 Hz, 2H, CH$_2$F; 5.94, dd, J=5 Hz and 8 Hz, 1H, β-lactam; 8.30, s, 1H, CH=N; 9.84, d, J=8 Hz, 1H, NH 11 1.15-1.58, m, 4H, CCH$_2$; 1.65-2.30, m, 4H, CCH$_2$; 2.92, s, 3H, NCH$_3$; 3.08-3.75, m, 3H, 2H from NCH and 1H from SCH$_2$; 4.48, part of the AB-quartet, J=18 Hz, 1H, SCH$_2$; 5.32, d, J=5 Hz, 1H, β-lactam; 5.77, d, J=55 Hz, 2H, CH$_2$F; 5.95, dd, J=5 Hz and 8 Hz, 1H, β-lactam; 8.52, s, 1H, CH=N; 9.82, d, J=8 Hz, 1H, NH 12 1.40-1.75, m, 4H, CCH$_2$; 1.92-2.32, m, 4H, CCH$_2$; 3.04, b, 9H, NCH$_3$; 3.25-3.80, m, 6H, 3H from NCH$_3$ and 2H from NCH and 1H from SCH$_2$; 4.58, part of the AB-quartet, J=18 Hz, 1H, SCH$_2$; 5.27, d, J=5 Hz, 1H, β-lactam; 5.78, d, J=55 Hz, 2H, CH$_2$F; 5.96, dd, J=5 Hz and 8 Hz, 1H, β-lactam; 8.07, s, 1H, CH=N; 9.86, d, J=8 Hz, 1H, NH 1.10-1.45, m, 4H, CCH$_2$; 1.55-1.88, m, 4H, CCH$_2$; 2.65-2.95, m, 1H, NCH; 3.28, s, 3H, NCH$_3$; 3.32-3.60, m, 2H, 1H from NH and 1H from SCH$_2$; 4.50, part of the AB-quartet, J=18 Hz, 1H, SCH$_2$; 5.26, d, J=5 Hz, 1H, β-lactam; 5.77, d, J=55 Hz, 2H, CH$_2$F; 5.96, dd, J=5 Hz and 8 Hz, 1H, β-lactam; 6.60, d, J=9 Hz, 2H, aromabc-H; 7.42, d, J=9 Hz, 2H, aromatic-H; 8.07, s, 1H, CH=N; 9.75, d, J=8 Hz, 1H, NH 14 1.30-1.58, m, 2H, CCH$_2$; 1.62-1.88, m, 4H, CCH$_2$; 2.00-2.22, m, 2H, CCH$_2$; 2.54, s, 3H, NCH$_3$; 2.72-3.10, m, 7H, 6H from NCH$_3$ and 1H from NCH; 3.48-3.72, m, 2H, 1H from NCH and 1H from SCH$_2$; 4.10, part of the AB-quartet, J=18 Hz, 1H, SCH$_2$; 5.28, d, J=5 Hz, 1H, β-lactam; 5.77, d, J=55 Hz, 2H, CH$_2$F; 5.94, dd, J=5 Hz and 8 Hz, 1H, β-lactam; 8.47, s, 1H, CH=N; 9.84, d, J=8 Hz, 1H, NH 15 1.30-1.70, m, 4H, CCH$_2$; 1.72-2.10, m, 4H, CCH$_2$; 2.70-3.10, m, 4H, 3H from NCH$_3$ and 1H from NCH; 3.35-3.70, m, 2H, 1H from NCH and 1H from SCH$_2$; 3.50, part of the AB-quartet, J=18 Hz, 1H, SCH$_2$; 5.28, d, J=5 Hz, 1H, β-lactam; 5.78, dd, J=55 Hz, 2H, CH$_2$F; 5.94, dd, J=5 Hz and 8 Hz, 1H, β-lactam; 8.55, s, 1H, CH=N; 9.85, d, J=8 Hz, 1H, NH 16 1.32-1.70, m, 4H, CCH$_2$; 1.80-2.20, m, 4H, CCH$_2$; 2.70, b, 6H, NCH$_3$; 2.88, d, 3H, NCH$_3$; 3.00-3.20, m, 1H, NCH; 3.38-3.70, m, 2H, 1H from NCH and 1H from SCH$_2$; 4.52, part of the AB-quartet, J=18 Hz,1H, SCH$_2$; 5.29, d, J=5 Hz, 1H, β-lactam; 5.78, d, J=55 Hz, 2H, CH$_2$F; 5.94, dd, J=5 Hz and 8 Hz, 1H, β-lactam; 8.28, b, 2H, NH$_2$; 8.63, s, 1H, CH=N; 9.84, d, J=8 Hz, 1H, NH 17 1.40-1.70, m, 4H, CCH$_2$; 1.88-2.30, m, 4H, CCH$_2$; 2.88, d, 3H, NCH$_3$; 3.08, b, 9H, NCH$_3$; 3.20-3.80, m, 3H, 2H from NCH and 1H from SCH$_2$; 4.51, part of the AB-quartet, J=18 Hz, 1H, SCH$_2$; 5.29, d, J=5 Hz, 1H, β-lactam; 5.78, d, J=55 Hz, 2H, CH$_2$F; 5.95, dd J=5 Hz and 8 Hz, 1H, β-lactam; 8.30, b, 2H, NH$_2$; 8.68, s, 1H, CH=N; 9.84, d, J=8 Hz, 1H, NH 18 1.10-2.22, m, 8H, CCH$_2$; 2.90, d, 3H, NCH$_3$; 3.08-3.32, m, 1H, NCH; 3.40-3.80, m, 2H, 1H from NCH and 1H from SCH$_2$; 3.54, part of the AB-quartet, J=18 Hz, 1H, SCH$_2$; 5.30, d, J=5 Hz,1H, β-lactam; 5.77, d, J=55 Hz, 2H, CH$_2$F; 5.96, dd, J=5 Hz and 8 Hz, 1H, β-lactam; 8.52, s, 1H, CH=N; 9.86, d, J=8 Hz, 1H, NH 19 1.30-1.75, m, 8H, CCH$_2$; 1.80-2.20, m, 8H, CCH$_2$; 2.80-3.20, m, 2H, NCH; 3.28, s, 3H, NCH$_3$; 3.40-3.75, m, 3H, 2H from NCH and 1H from SCH$_2$; 4.20, part of the AB-quartet, J=18 Hz, 1H, SCH$_2$; 5.15, d, J=5 Hz, 1H, β-lactam; 5.76, dd, J=5 Hz and 8 Hz, 1H, β-lactam; 5.79, d, J=55 Hz, 2H, CH$_2$F; 8.09, s, 1H, CH=N; 9.84, d, J=8 Hz, 1H, NH 20 1.02-2.20, m, 8H, CCH$_2$; 2.90-3.18, m, 1H, NCH; 3.32, s, 3H, NCH$_3$; 3.42-3.78, m, 2H, 1H from NCH and 1H from SCH$_2$; 3.55, part of the AB-quartet, J=18 Hz, 1H, SCH$_2$; 5.28, d, J=5 Hz, 1H, β-lactam; 5.78, d, J=55 Hz, 2H, CH$_2$F; 5.94, dd, J=5 Hz and 8 Hz, 1H, β-lactam; 8.12, s, 1H, CH=N; 9.82, d, J=8 Hz, 1H, NH 21 1.10-2.22, m, 8H, CCH$_2$; 3.00-3.18, m, 1H, NCH; 3.35, b, 3H, NCH$_3$; 3.45-3.82, m, 1.5H, 1H from SCH$_2$ and 0.5H from NCH; 4.10-4.30, m, 0.5H, NCH; 3.54, part of the AB-quartet, J=18 Hz, 0.5H, SCH$_2$; 3.62, part of the AB-quartet, J=18 Hz, 0.5H, SCH$_2$; 5.12-5.22, m, 1H, β-lactam; 5.70-5.85, m, 1H, β-lactam; 5.78, d, J=5 Hz, 2H, CH$_2$F; 8.10, b, 1H, CH=N; 9.77, d, J=8 Hz, 1H, NH 22 1.08-1.62, m, 4H, CCH$_2$; 1.70-2.25, m, 4H, CCH$_2$; 2.90-3.20, m, 1H, NCH; 3.32, b, 3H, NCH$_3$; 3.42-3.82, m, 2H, 1H from NCH and 1H from SCH$_2$; 4.45-4.70, m, 1H, SCH$_2$; 5.10-5.28, m, 1H, β-lactam; 5.65-5.90, m, 1H, β-lactam; 5.78, d, J=55 Hz, 2H, CH$_2$F; 8.10, b, 1H, CH=N; 9.85, d, J=8 Hz, 1H, NH 23 1.30-2.00, m, 7H, CCH$_2$; 2.10-2.30, m, 1H, CCH$_2$; 3.25-3.62, m, 5H, 3H from NCH$_3$, 1H from NCH and 1H from SCH$_2$; 3.98-4.18, m, 1H, NCH; 4.53, part of the AB-quartet, J=18 Hz, 1H, SCH$_2$; 5.18, d, J=5 Hz, 1H, β-lactam; 5.78, dd, J=5 Hz and 8 Hz, 1H, β-lactam; 5.79, d, J=55 Hz, 2H, CH$_2$F; 8.11, s, 1H, CH=N; 9.75, d, J=8 Hz, 1H, NH 24 1.30-1.70, m, 10H, 4H from CCH$_2$ and 6H from CCH$_3$; 1.82-2.12, m, 4H, CCH$_2$; 2.88-3.12, m, 1H, NCH; 3.29, s, 3H, NCH$_3$; 3.42-3.70, m, 2H, 1H from NCH and 1H from SCH$_2$; 4.48, part of the AB-quartet, J=18 Hz,1H, SCH$_2$; 5.32, d, J=5 Hz, 1H, β-lactam; 5.98, dd, J=5 Hz and 8Hz, 1H, β-lactam; 7.06, s, 1H, CH thiazol; 8.11, s, 1H, CH=N; 9.68, d, J=8 Hz, 1H, NH 25 1.22-1.70, m, 4H, CCH$_2$; 1.82-2.18, m, 4H, CCH$_2$; 2.88-3.18, m, 1H, NCH; 3.45-3.80, m, 4H, 3H from NCH$_3$ and 1H from SCH$_2$; 3.96-4.28, m, 1H, NCH; 4.48, part of the AB-quartet, J=18 Hz, 1H, SCH$_2$; 5.25, d, J=5 Hz, 1H, β-lactam; 5.78, d, J=55 Hz, 2H, CH$_2$F; 5.96, dd, J=5 Hz and 8 Hz, 1H, β-lactam; 8.02, s, 1H, CH=N; 9.86, d, J=8 Hz, 1H, NH 26 1.30-1.60, m, 4H, CCH$_2$; 1.70-2.05, m, 4H, CCH$_2$; 2.80-3.05, m, 1H, NCH; 3.18, s, 3H, NCH$_3$; 3.38-3.68, m, 2H, 1H from NCH and 1H from SCH$_2$; 4.48, part of the AB-quartet, J=18 Hz, 1H, SCH$_2$; 5.22, d, J=5 Hz, 1H, β-lactam; 5.76, d, J=55 Hz, 2H, CH$_2$F; 5.92, dd, J=5 Hz and 8Hz, 1H, β-lactam; 7.85, s, 1H, CH=N; 9.82, d, J=8 Hz, 1H, NH 27 1.10-1.65, m, 4H, CCH$_2$; 1.72-2.25, m, 4H, CCH$_2$; 2.88-3.18, m, 1H, NCH; 3.32, s, 3H, NCH$_3$; 3.42-3.80, m, 2H, 1H from NCH and 1H from SCH$_2$; 4.54, part of the AB-quartet, J=18 Hz, 1H, SCH$_2$; 5.17, d, J=5 Hz, 1H, β-lactam; 5.77, dd, J=5 Hz and 8 Hz, 1H, β-lactam; 5.78, d, J=55 Hz, 2H, CH$_2$F; 8.10, s, 1H, CH=N; 9.85, d, J=5 Hz, 1H, NH 28 1.28-1.68, m, 4H, CCH$_2$; 1.88-2.15, m, 4H, CCH$_2$; 2.72-3.08, m, 4H, 3H from NCH$_3$ and 1H from NCH; 3.28, s, 3H, NCH$_3$; 3.40-3.72, m, 2H, 1H from NCH and 1H from SCH$_2$; 4.25, part of the AB-quartet, J=18 Hz, 1H, SCH$_2$; 5.27, d, J=5 Hz, 1H, β-lactam; 5.78, d, J=55 Hz, 2H, CH$_2$F; 5.94, dd, J=5 Hz and 8 Hz, 1H, β-lactam; 8.06, s, 1H, CH=N; 9.85, d, J=8 Hz,1H, NH 29 (500 MHz, CDCl$_3$/CH$_3$OD) 0.82-0.88, m, 2H, CCH$_2$; 1.32-2.14, m, 10H, CCH$_2$; 2.68-2.82, m, 2H, NCH; 3.52-3.72, m, 2H, 1H from SCH$_2$ and 1H from NCH; 4.12, part of the AB-quartet, J=18 Hz, 1H, SCH$_2$; 5.15, d, J=5 Hz, 1H, β-lactam; 5.78, d, J=55 Hz, 2H, CH$_2$F; 5.96, d, J=5 Hz, 1H, β-lactam; 8.65, s, 1H, CH=N 30 1.38-2.15, m, 8H, CCH$_2$; 2.78-3.10, m, 7H, 6H from NCH$_3$ and 1H from NCH; 3.35-3.70, m, 2H, 1H from SCH$_2$ and 1H from NCH; 4.11, part of the AB-quartet, J=18 Hz, 1H, SCH$_2$; 5.28, d, J=5 Hz, 1H, β-lactam; 5.77, d, J=55 Hz, 2H, CH$_2$F; 5.94, dd, J=5 Hz and 8 Hz, 1H, β-lactam; 8.47, s, 1H, CH=N; 9.85, d, J=8 Hz, 1H, NH 31 1.28-2.10, m, 8H, CCH$_2$; 2.80-3.10, m, 7H, 6H from NCH$_3$ and 1H from NCH; 3.40-3.70, m, 2H, 1H from SCH$_2$ and 1H from NCH; 4.12, part of the AB-quartet, J=18 Hz, 1H, SCH$_2$; 5.29, d, J=5 Hz, 1H, 1-lactam; 5.78, d, J=55 Hz, 2H, CH$_2$F; 5.94, dd, J=5 Hz and 8Hz, 1H, β-lactam; 8.47, s, 1H, CH=N; 9.85, d, J=8 Hz, 1H, NH 32 (D$_2$O) 1.65-2.15, m, 8H, CCH$_2$; 2.75-3.05, m, 6H, NCH$_3$; 3.22, s, 3H, NCH$_3$; 3.40-3.70, m, 3H, 2H from NCH and 1H from SCH$_2$; 3.90, part of the AB-quartet, J=18 Hz, 1H, SCH$_2$; 5.22, d, J=5 Hz,1H, β-lactam; 5.76, d, J=55 Hz, 2H, CH$_2$F; 5.80, d, J=5 Hz, 1H, β-lactam; 7.90, s, 1H, CH=N 33 (D$_2$O) 1.25-1.60, m, 4H, CCH$_2$; 1.90-2.25, m, 4H, CCH$_2$; 3.00-3.28, m, 4H, 3H from NCH$_3$ and 1H from NCH; 3.35-3.68, m, 4H, 2H from NCH$_2$ and 1H from SCH$_2$ and 1H from NCH; 3.95, part of the AB-quartet, J=18 Hz, 1H. SCH$_2$; 5.22, d, J=5 Hz, 1H, β-lactam; 5.30-5.50, m, 2H, CH$_2$=C; 5.74, d, J=55 Hz, 2H, CH$_2$F; 5.65-5.88, m, 2H, 1H from CH=C and 1H from β-lactam; 7.89, s, 1H, CH=N 34 (D$_2$O) 1.30-1.80, m, 4H, CCH$_2$; 1.98-2.20, m, 4H, CCH$_2$; 3.20, s, 3H, NCH$_3$; 3.30-4.05, m, 8H, 4H from NCH$_2$ and 2H from NCH and 2H from SCH$_2$; 5.21, d, J=5 Hz, 1H, β-lactam; 5.40-5.98, m, 9H, 4H from CH$_2$=C and 2H from CH=C and 2H from CH$_2$F and 1H from β-lactam; 7.89, s, 1H, CH=N 35 (D$_2$O) 1.10-1.65, m, 16H, 4H from CCH$_2$ and 12H from CH$_3$; 1.90-2.20, m, 4H, CCH$_2$; 3.05-3.30, m, 4H, 3H from NCH$_3$ and 1H from NCH; 3.35-3.60, m, 3H, 2H from NCH and 1H from SCH$_2$; 3.65-4.05, m, 2H, 1H from SCH$_2$ and 1H from NCH; 5.22, d, J=5 Hz, 1H, β-lactam; 5.75, d, J=55 Hz, 2H, CH$_2$F; 5.78, d, J=5 Hz, 1H, β-lactam; 7.90, s, 1H, CH=N 36 (D$_2$O) 1.20, d, J=6 Hz, 6H, CH$_3$; 1.30-1.65, m, 4H, CCH$_2$; 1.90-2.20, m, 4H, CCH$_2$; 3.05-3.30, m, 4H, 3H from NCH$_3$ and 1H from NCH; 3.35-3.68, m, 3H, 1H from SCH$_2$ and 2H from NCH; 3.95, part of the AB-quartet, J=18 Hz, 1H, SCH$_2$; 5.21, d, J=5 Hz, 1H, β-lactam; 5.74, d, J=5 Hz, 1H, β-lactam; 5.75, d, J=55 Hz, 2H, CH$_2$F; 7.89, s, 1H, CH=N 37 (D$_2$O) 1.16, t, J=7 Hz, 3H, CH$_3$; 1.30-1.60, m, 4H, CCH$_2$; 1.92-2.25, m, 4H, CCH$_2$; 2.90-3.30, m, 6H, 3H from NCH$_3$ and 2H from NCH$_2$ and 1H from NCH; 3.32-3.65, m, 2H, 1H from SCH$_2$ and 1H from NCH; 3.95, part of the AB-quartet, J=18 Hz, 1H, SCH$_2$; 5.21, d, J=5 Hz, 1H, β-lactam; 5.73, d, J=55 Hz, 2H, CH$_2$F; 5.74, d, J=5 Hz, 1H, β-lactam; 7.89, s, 1H, CH=N 38 (D$_2$O) 1.21, t, J=7 Hz, 6H, CH$_3$; 1.35-1.75, m, 4H, CCH$_2$; 1.90-2.20, m, 4H, CCH$_2$; 2.92-3.70, m, 10H, 3H from NCH$_3$ and 4H from NCH$_2$ and 2H from NCH and 1H from SCH$_2$; 3.93, part of the AB-quartet, J=18 Hz, 1H, SCH$_2$; 5.21, d, J=5 Hz, 1H, β-lactam; 5.72, d, J=5 Hz, 1H, β-lactam; 5.74, d, J=55 Hz, 2H, CH$_2$F; 7.89, s, 1H, CH=N 39 (D$_2$O) 0.86, t, J=7 Hz, 3H, CH$_3$; 1.30-1.70, m, 6H, CCH$_2$; 1.90-2.28, m, 4H, CCH$_2$; 2.80-3.28, m, 6H, 3H from NCH$_3$ and 2H from NCH$_2$ and 1H from NCH; 3.32-3.62, m, 2H, 1H from NCH and 1H from SCH$_2$; 3.93, part of the AB-quartet, J=18 Hz, 1H, SCH$_2$; 5.21, d, J=5 Hz, 1H, β-lactam; 5.73, d, J=55 Hz, 2H, CH$_2$F; 5.74, d, J=5 Hz, 1H, β-lactam; 7.89, s, 1H, CH=N 40 (D$_2$O) 0.86, t, J=7 Hz, 6H, CH$_3$; 1.30-1.78, m, 8H, CCH$_2$; 1.92-2.22, m, 4H, CCH$_2$; 2.82-3.65, m, 10H, 3H from NCH$_3$ and 4H from NCH$_2$ and 2H from NCH and 1H from SCH$_2$; 3.96, part of the AB-quartet, J=18 Hz, 1H, SCH$_2$; 5.21, d, J=5 Hz, 1H, β-lactam; 5.73, d, J=55 Hz, 2H, CH$_2$F; 5.74, d, J=5 Hz, 1H, β-lactam; 7.92, s, 1H, CH=N 41 (D$_2$O) 1.28-1.65, m, 4H, CCH$_2$; 1.95-2.25, m, 4H, CCH$_2$; 2.60, s, 3H, NCH$_3$; 2.90-3.15, m, 1H, NCH; 3.20, s, 3H, NCH$_3$; 3.32-3.65, m, 2H, 1H from NCH and 1H from SCH$_2$; 3.95, part of the AB-quartet, J=18 Hz, 1H, SCH$_2$; 5.21, d, J=5 Hz, 1H, β-lactam; 5.73, d, J=55 Hz, 2H, CH$_2$F; 5.74, d, J=5 Hz, 1H, β-lactam; 7.89, s, 1H, CH=N 42 (D$_2$O) 1.32-2.25, m, 8H, CCH$_2$; 2.75-3.28, m, 4H, 3H from NCH$_3$ and 1H from NCH; 3.40-3.85, m, 2H, 1H from NCH and 1H from SCH$_2$; 3.95, part of the AB-quartet, J=18 Hz, 1H, SCH$_2$; 5.22, d, J=5 Hz, 1H, β-lactam; 5.75, d, J=55 Hz, 2H, CH$_2$F; 5.76, d, J=5 Hz, 1H, β-lactam; 8.18, s, 1H, CH=N 43 (D$_2$O) 1.28-2.20, m, 8H, CCH$_2$; 2.81, s, 3H, NCH$_3$; 3.05-3.30, m, 4H, 3H from NCH$_3$ and 1H from NCH; 3.40-3.70, m, 2H, 1H from NCH and 1H from SCH$_2$; 3.95, part of the AB-quartet, J=18 Hz, 1H, SCH$_2$; 5.22, d, J=5 Hz, 1H, β-lactam; 5.75, d, J=55 Hz, 2H, CH$_2$F; 5.79, d, J=5 Hz, 1H, β-lactam; 7.90, s, 1H, CH=N

The invention claimed is:

1. A compound of formula

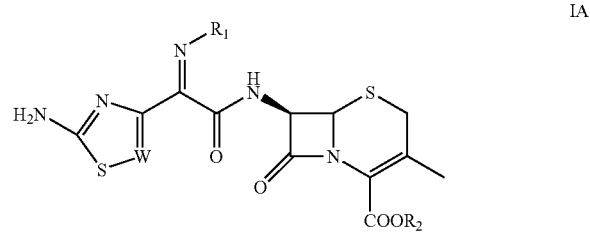

IA or of formula

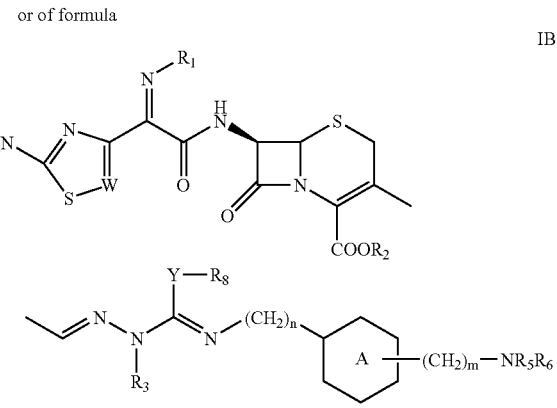

IB wherein

W is CH or N,

R$_1$ is hydroxy, (C$_{1-6}$)alkoxy, halo(C$_{1-6}$)alkoxy, hydroxycarbonyl(C$_{1-6}$)alkoxy or (C$_{1-6}$)alkoxycarbonyl(C$_{1-6}$)alkoxy, R$_2$ is hydrogen or an ester moiety, R$_3$ is hydrogen, (C$_{1-6}$)alkyl, (C$_{2-6}$)alkenyl or (C$_{3-8}$)cycloalkyl, $R_4$ is hydrogen or $(C_{1-6})$alkyl,

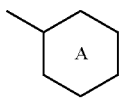

is cyclohexyl or phenyl, $R_5$ and $R_6$ independently of each other are hydrogen; $(C_{1-6})$alkyl; $(C_{2-6})$alkenyl; $(C_{6-18})$arylcarbonyl; $(C_{1-6})$alkylcarbonyl; $(C_{6-18})$aryloxy$(C_{1-4})$alkylcarbonyl; $(C_{1-6})$alkylcarbonyl -$(C_{6-18})$arylcarbonyl; heterocyclyl$(C_{1-6})$alkylcarbonyl, wherein heterocyclyl comprises 5 or 6 ring members and 1 to 4 heteroatoms selected from N, O or S; $(C_{1-6})$alkylsulfonyl or $(C_{6-18})$arylsulfonyl, X is NH, O, S or N—$R_8$, wherein $R_8$ is $(C_{1-6})$alkyl or $(C_{3-8})$cycloalkyl, Y is O or S, and n and m independently of each other are 0 or 1.

2. The compound of claim 1 wherein

W is CH or N, $R_1$ is hydroxy, methoxy, fluoromethoxy or (hydroxycarbonyl)(dimethyl)methoxy, $R_2$ is hydrogen, $R_3$ is hydrogen; $(C_{1-4})$alkyl, e.g. methyl or ethyl; allyl or cyclopropyl, $R_4$ is hydrogen or $(C_{1-4})$alkyl, e.g. methyl,

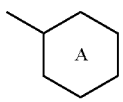

is cyclohexyl, e.g. and the —$(CH_2)_m$—$NR_5R_6$ group is in the ortho, meta or para position, $R_5$ and $R_6$ independently of each other are hydrogen; $(C_{1-3})$alkyl; allyl; $(C_{1-4})$alkylcarbonyl; phenylcarbonyl, wherein phenyl is optionally substituted by $(C_{1-4})$alkylcarbonyloxy; phenyoxymethylcarbonyl; phenylsulfonyl, wherein phenyl is substituted by amino or $(C_{1-4})$alkylcarbonylamino, or heterocyclyl comprising 5 ring members and 1 heteroatom selected from N, O or S, X is NH, NCH$_3$, NCH(CH$_3$)$_2$, O, S or $(C_{3-8})$cycloalkyl substituted by amino, n is 0, m is 0, Y is S and $R_8$ is $C_{1-4}$alkyl.

3. The compound of claim 1 wherein in formula IA

W is N or CH, $R_1$ is hydroxy or fluoromethoxy, $R_2$, $R_4$, $R_5$ and $R_6$ are hydrogen, $R_3$ is $C_{1-4}$alkyl,

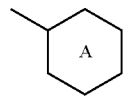

is cyclohexyl,

X is NH, n is 1 and m is 1.

4. The compound of claim 1 wherein in formula IA

W is N, $R_1$ is fluoromethoxy, $R_2$, $R_4$, $R_5$ and $R_6$ are hydrogen, $R_3$ is $C_{1-4}$alkyl, is phenyl, X is NH, n is 1 and m is 0.

5. The compound of claim 1 wherein in formula IA

W is CH or N, $R_1$ is hydroxy or fluoromethoxy, $R_2$, $R_4$, $R_5$ and $R_6$ are hydrogen, $R_3$ is $C_{1-4}$alkyl,

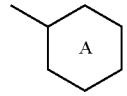

is phenyl,

X is NH, n is 1 and m is 1.

6. A compound of formula

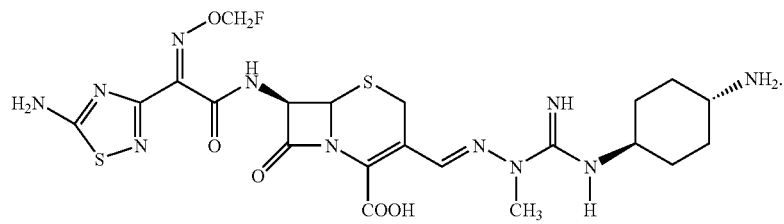

7. A compound in the form of a salt, said compound being a compound of formula

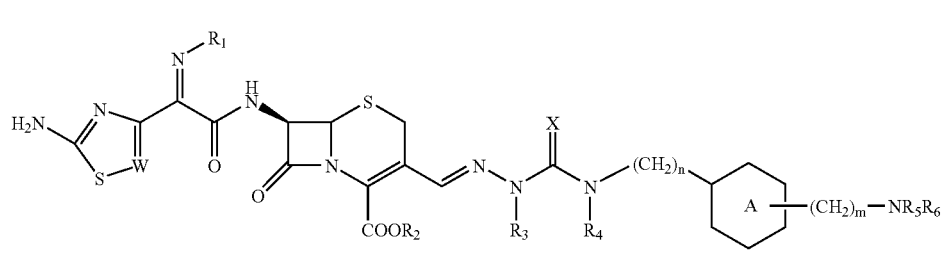

IA or of formula

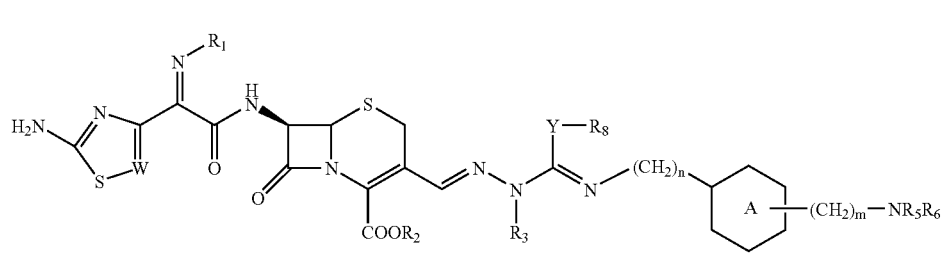

IB wherein

W is CH or N, $R_1$ is hydroxy, $(C_{1-6})$alkoxy, halo$(C_{1-6})$alkoxy. hydroxycarbony$(C_{1-6})$alkoxy or $(C_{1-6})$alkoxycarbonyl$(C_{1-6})$alkoxy, $R_2$ is hydrogen or an ester moiety, $R_3$ is hydrogen, $(C_{1-6})$alkyl, $(C_{2-6})$alkenyl or $(C_{3-8})$cycloalkyl, $R_4$ is hydrogen or $(C_{1-6})$alkyl,

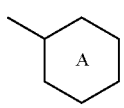

is cyclohexyl or phenyl, $R_5$ and $R_6$ independently of each other are hydrogen; $(C_{1-6})$alkyl; $(C_{2-6})$alkenyl;

$(C_{6-18})$arylcarbonyl; $(C_{1-6})$alkylcarbonyl; $(C_{6-18})$aryloxyl $(C_{1-4})$alkylcarbonyl; $(C_{1-6})$alkylcarbonyl- $(C_{6-18})$arylcarbonyl; heterocyclyl$(C_{1-6})$alkylcarbonyl, wherein heterocyclyl comprises 5 or 6 ring members and 1 to 4 heteroatoms selected from N, O or S; $(C_{1-6})$alkylsulfonyl or $(C_{6-18})$arylsulfonyl, X is NH, O, S or N-$R_8$, wherein $R_8$ is $(C_{1-6})$alkyl or $(C_{3-8})$ cycloalkyl, Y is O or S, and n and m independently of each other are 0 or 1.

8. A pharmaceutical composition comprising a compound according to claim 1 in association with at least one pharmaceutical excipient.

9. A method of treatment of microbial diseases which comprises administering to a subject in need of such treatment an effective amount of a compound according to claim 1.

10. A process for preparing a compound of formula IA

*[Structure IA shown]* or a compound of formula IB

*[Structure IB shown]* said process comprising reacting a compound of formula III

*[Structure III shown]* with a compound of formula IVA

*[Structure IVA shown]* or a compound of formula IVB

*[Structure IVB shown]* wherein
W is CH or N,
$R_1$ is hydroxy, $(C_{1-6})$alkoxy, halo$(C_{1-6})$alkoxy, hydroxycarbonyl$(C_{1-6})$alkoxy or $(C_{1-6})$alkoxycarbonyl$(C_{1-6})$alkoxy,
$R_2$ is hydrogen or an ester moiety,
$R_3$ is hydrogen, $(C_{1-6})$alkyl, $(C_{2-6})$alkenyl or $(C_{3-8})$cycloalkyl,
$R_4$ is hydrogen or $(C_{1-6})$alkyl,

*[Structure A (cyclohexyl) shown]* is cyclohexyl or phenyl,
$R_5$ and $R_6$ independently if each other are hydrogen; $(C_{1-6})$alkyl; $(C_{2-6})$alkenyl; $(C_{6-18})$arylcarbonyl; $(C_{1-6})$alkylcarbonyl; $(C_{6-18})$aryloxy$(C_{1-4})$alkylcarbonyl; $(C_{1-6})$alkylcarbonyl-$(C_{6-18})$arylcarbonyl; heterocyclyl$(C_{1-6})$alkylcarbonyl; wherein heterocyclyl comprises 5 or 6 ring members and 1 to 4 heteroatoms selected from N, O or S; $(C_{1-6})$alkylsulfonyl or
$(C_{6-18})$arylsulfonyl,
X is NH, O, S or N-$R_8$, wherein $R_8$ is $(C_{1-6})$alkyl or $(C_{3-8})$cycloalkyl,
Y is O or S, and n and m independently of each other are 0 or 1.

* * * * *